US009131307B2

(12) United States Patent
Teranishi

(10) Patent No.: US 9,131,307 B2
(45) Date of Patent: Sep. 8, 2015

(54) NOISE ELIMINATING DEVICE, NOISE ELIMINATING METHOD, AND NOISE ELIMINATING PROGRAM

(71) Applicant: JVC KENWOOD Corporation, Yokohama-shi (JP)

(72) Inventor: Yasuhiko Teranishi, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 132 days.

(21) Appl. No.: 14/103,631

(22) Filed: Dec. 11, 2013

(65) Prior Publication Data

US 2014/0161271 A1 Jun. 12, 2014

(30) Foreign Application Priority Data

Dec. 11, 2012 (JP) ................................ 2012-270114
Feb. 27, 2013 (JP) ................................ 2013-036810
Apr. 30, 2013 (JP) ................................ 2013-095067

(51) Int. Cl.
*A61F 11/06* (2006.01)
*H04R 5/04* (2006.01)

(52) U.S. Cl.
CPC .............. *H04R 5/04* (2013.01); *H04R 2410/07* (2013.01)

(58) Field of Classification Search
CPC .................................................. G10K 11/1788
USPC ........................................................ 381/71.1
See application file for complete search history.

(56) References Cited

U.S. PATENT DOCUMENTS

2008/0013617 A1* 1/2008 Ooi .............................. 375/232

FOREIGN PATENT DOCUMENTS

| | | |
|---|---|---|
| JP | 05-161191 | 6/1993 |
| JP | 06-269083 | 9/1994 |
| JP | 2005-303681 | 10/2005 |
| JP | 2006-506929 | 2/2006 |
| JP | 2009-036831 | 2/2009 |
| WO | WO-2004/045175 | 5/2004 |

OTHER PUBLICATIONS

Xiaohua et al., "Block Implementation of Adaptive IIR Filter," Proceedings of the Institute of Electronics, Information, and Communication Engineers General Conference, Engineering Sciences, p. 182 (1996).

* cited by examiner

*Primary Examiner* — Simon King
(74) *Attorney, Agent, or Firm* — Venable LLP; Michael A. Sartori

(57) ABSTRACT

Provided is a noise eliminating device that includes: a signal calculator that calculates a difference signal between a signal of one channel out of a plurality of signals input from a plurality of channels and a signal of another channel; a variable filter unit that processes and outputs the signals of channels; an adaptive filter unit that operates by receiving a composite signal of the difference signal and another signal as an input signal; and a unit that calculates an error signal between an output signal of the adaptive filter unit and a signal having correlation with the another signal being set as a desired signal. Characteristics of the adaptive filter are changed by using the error signal. Further, characteristics of the variable filter are changed in accordance with a change in the characteristics of the adaptive filter.

21 Claims, 15 Drawing Sheets

NOISE ELIMINATING DEVICE, NOISE ELIMINATING METHOD, AND NOISE ELIMINATING PROGRAM

CROSS-REFERENCE TO RELATED APPLICATIONS

The present application claims priority to and incorporates by reference the entire contents of Japanese Patent Application No. 2012-270114 filed in Japan on Dec. 11, 2012; Japanese Patent Application No. 2013-036810 filed in Japan on Feb. 27, 2013; and Japanese Patent Application No. 2013-095067 filed in Japan on Apr. 30, 2013.

BACKGROUND OF THE INVENTION

1. Field of the Invention

The present invention relates to a noise eliminating device, a noise eliminating method, and a noise eliminating program.

2. Description of the Related Art

In Japanese Patent Application Publication Laid-open No. 5-161191 and Japanese Patent Application Publication Laid-open No. 6-269083, methods using adaptive filters are disclosed. FIG. 7 illustrates a conceptual diagram of an adaptive filter. Generally, an adaptive filter 10 performs a filter operation for an input signal $X_n$ of discrete time n and outputs an output signal $Y_n$. A subtracter 30 to which the output signal $Y_n$ has been input outputs an error signal $E_n$ that represents a difference between a desired signal $D_n$ and the output signal $Y_n$; and the adaptive filter 10 changes the filter characteristics such that the error signal $E_n$ decreases. Then, by using the changed filter characteristics, the filter operation is performed for an input signal $X_{n+1}$ of the next discrete time n+1. Thereafter, the process is repeated.

FIG. 8 is a configuration diagram that illustrates a case where a filter is implemented as a finite impulse response (FIR) filter. This adaptive filter 10 is equipped with a variable filter 11 that performs an FIR filter operation and a filter coefficient generator 12 that updates the coefficients of the variable filter 11 based on an adaptive algorithm. The variable filter 11 is equipped with: a plurality of delay devices 101, 102, . . . , 103 that delay the input signal $X_n$; multipliers 111, 112, . . . , 113 that respectively multiply the input signal $X_n$ and delay signals $X_{n-1}$, $X_{n-2}$, . . . , $X_{n-(m-n)}$, which are acquired by delaying the input signal, by coefficients $W_0$, $W_1$, . . . , $W_{m-1}$ that are set by the filter coefficient generator 12; and an adder 120 that adds the outputs of the multipliers and outputs an output signal $Y_n$.

As the adaptive algorithm (the algorithm for adjusting the coefficients of the adaptive filter), a least mean square (LMS) algorithm is frequently used. Alternatively, instead of the LMS algorithm, a recursive least square (RLS) algorithm or the like may be used.

In addition, instead of the FIR filter, there is a case where an infinite impulse response (IIR) filter is used (see, Wu and Others, "Block Implementation of Adaptive IIR Filter", Proceedings of the Institute of Electronics, Information and Communication Engineers General Conference, 1996, Engineering Sciences, 182, 1996-03-11, or the like). Furthermore, there is also a case where an input signal is transformed into a frequency-domain signal, and an adaptive filter operation is performed in the frequency domain (see Japanese Patent Application Publication (Translation of PCT Application) No. 2006-506929 W or the like).

According to Japanese Patent Publication Laid-open No. 5-161191, a signal that is acquired by delaying a signal received by one microphone is set as a desired signal input of the adaptive filter; a difference signal between the signal received by the microphone and a signal received by another microphone arranged closely thereto is set as an input signal; and an error signal is set as an output signal of a noise canceller. In addition, according to Japanese Patent Publication Laid-open No. 6-269083, a signal acquired by applying a band pass filter (BPF) to a signal received by one microphone is set as a desired signal input; and a signal acquired by applying a BPF to a difference signal is set as an input signal.

In a signal received by the one microphone, a wind noise n0 is mixed in a desired signal s. On the other hand, also in a signal received by the microphone that is arranged to be close thereto, a wind noise n0' is mixed in a desired signal s'. Here, in a case where the two microphones are arranged to be close to each other, the low-frequency components of the desired signals s and s' are almost the same.

On the other hand, the wind noises mixed into the two microphones do not have any correlation. Accordingly, as the output of the BPF of a difference signal between the signals of two microphone, $n1=(s+n0)-(s'+n0')=n0-n0'$, which represents only the wind noise. The adaptive filter is applied to the output signal n1; and the coefficients of the adaptive filter are updated such that a value acquired by subtracting a resultant signal from the delayed signal s+n0 of the one microphone is minimized. As a result, an expected value $E[n0-(n0-n0')]$ is minimized, whereby the desired signal s is acquired as the output.

However, practically, even when the adaptive filter is applied to the output signal $n1=n0-n0'$, it is difficult to acquire an estimated value of the signal n0 with high accuracy. The reason for this is that there is no correlation between n0 and n0', and the frequency components are distributed to be similar to each other. Accordingly, there is a problem in that the effect of reduction of the wind noise is not sufficient by using the methods disclosed in Japanese Patent Publication Laid-open No. 5-161191 and Japanese Patent Publication Laid-open No. 6-269083.

SUMMARY OF THE INVENTION

It is an object of the present invention to at least partially solve the problems in the conventional technology.

According to an aspect of the present invention, provided is a noise eliminating device that includes: a signal calculator that calculates a difference signal between a signal of one channel out of a plurality of signals input from a plurality of channels and a signal of another channel; a variable filter unit configured to process and output the signals of the plurality of channels; an adaptive filter unit configured to operate by receiving a composite signal of the difference signal and another signal as an input signal; and a unit configured to calculate an error signal between an output signal of the adaptive filter unit and a signal having correlation with the another signal being set as a desired signal. Characteristics of the adaptive filter are changed by using the error signal. Further, characteristics of the variable filter are changed in accordance with a change in the characteristics of the adaptive filter.

According to another aspect of the present invention, a noise eliminating method includes: calculating a difference signal between a signal of one channel out of a plurality of signals input from a plurality of channels and a signal of another channel; performing a variable filter process in which the signals of the plurality of channels are processed and output; calculating a composite signal of the difference signal and another signal; performing an adaptive filter process in which the composite signal is processed and output as an input signal; calculating an error signal between an output signal of an adaptive filter and a signal having correlation with the another signal being set as a desired signal; changing characteristics of the adaptive filter by using the error signal; and changing characteristics of the variable filter in accordance with a change in the characteristics of the adaptive filter.

According to still another aspect of the present invention, a noise eliminating program allows a computer to perform the noise eliminating method mentioned-above.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, noise eliminating devices according to preferred embodiments of the present invention will be described.

First Embodiment

Figure 1:
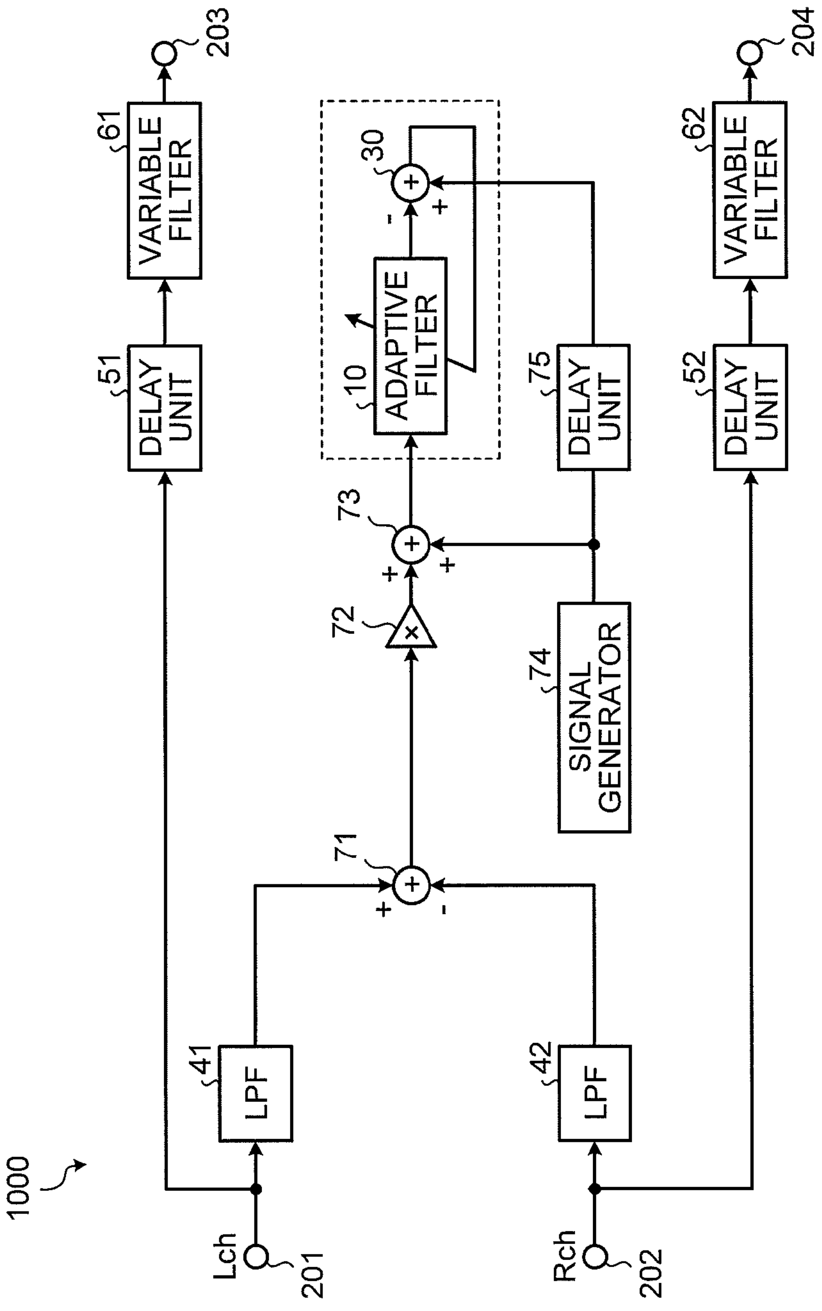
FIG. 1 is a configuration diagram of a noise eliminating device according to a first embodiment.

FIG. 1 is a diagram that illustrates the configuration of a noise eliminating device according to a first embodiment. Audio signals of right and left channels Rch and Lch of stereo transmitted from two microphones arranged in a casing of an electronic apparatus are converted from analog to digital, and the converted signals are input from input terminals.

Figure 7:
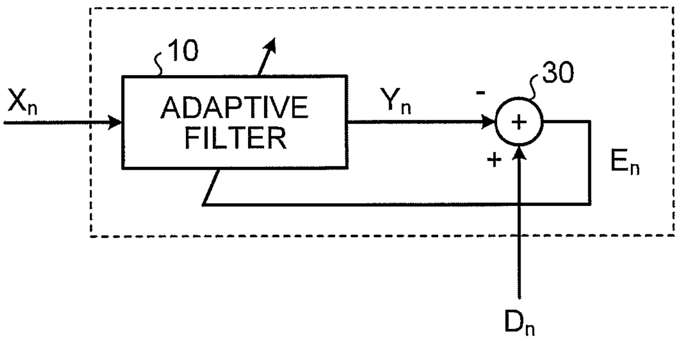
FIG. 7 is a configuration diagram of an adaptive filter in a conventional example.

A noise eliminating device 1000 is equipped with: an adaptive filter 10; a subtracter 30; a low pass filter (LPF) 41; an LPF 42; a delay unit 51; a delay unit 52; variable filters 61 and 62; a subtracter 71; a constant multiplier 72; an adder 73; a signal generator 74; a delay unit 75; input terminals 201 and 202; and output terminals 203 and 204. The adaptive filter 10 is similarly configured to a conventional example illustrated in FIG. 7.

The noise eliminating device 1000 may be realized by an analog circuit, a digital circuit, and the like, by software of a central processing unit (CPU), a digital signal processor (DSP), or the like, or by a combination thereof.

An audio signal of the left channel Lch received from the left microphone is input to the input terminal 201. An audio signal of the right channel Rch received from the right microphone is input to the input terminal 202. The audio signal of the left channel Lch is input to the delay unit 51 and the LPF 41. The audio signal of the right channel Rch is input to the delay unit 52 and the LPF 42. The outputs of the LPFs 41 and 42 are input to the subtracter 71. The subtracter 71 calculates a difference signal between the audio signals of the left and right channels Lch and Rch. The subtracter 71 serves as a signal calculator that calculates a difference signal between signals of two channels. In addition, the subtracter 71 serves as a unit that calculates a signal relating to a noise component based on input signals.

The difference signal is multiplied by ½ by the constant multiplier 72 and then is input to the adder 73. The other input of the adder 73 is the output of the signal generator 74. The output of the adder 73 is the input of the adaptive filter 10. The output of the adder 73 is a composite signal of the difference signal and another signal (a signal output from the signal generator 74). In addition, or in another way, the output is a composite signal of a signal relating to a noise component and the signal output from the signal generator 74. The output of the signal generator 74 is also input to the delay unit 75.

The output of the delay unit 75 is input to the subtracter 30 as a desired signal of the adaptive filter. The output of the delay unit 75 is a signal relating to another signal. The adaptive filter 10 and the subtracter 30 operate similarly to the conventional example illustrated in FIG. 7. In other words, the coefficients of the adaptive filter are varied such that an error signal that is a difference between the output of the adaptive filter and the desired signal decreases.

The output of the delay unit 51 is input to the variable filter 61; and the output of the variable filter 61 is output to the output terminal 203 as an output signal acquired by eliminating a wind noise from the audio signal of the left channel Lch. Similarly, the output of the delay unit 52 is input to the variable filter 62; and the output of the variable filter 62 is output to the output terminal 204 as an output signal acquired by eliminating a wind noise from the audio signal of the right channel Rch. The output signals output from the output terminals 203 and 204 are encoded by encoders not illustrated in the figure and are recorded in a recording medium.

Figure 8:
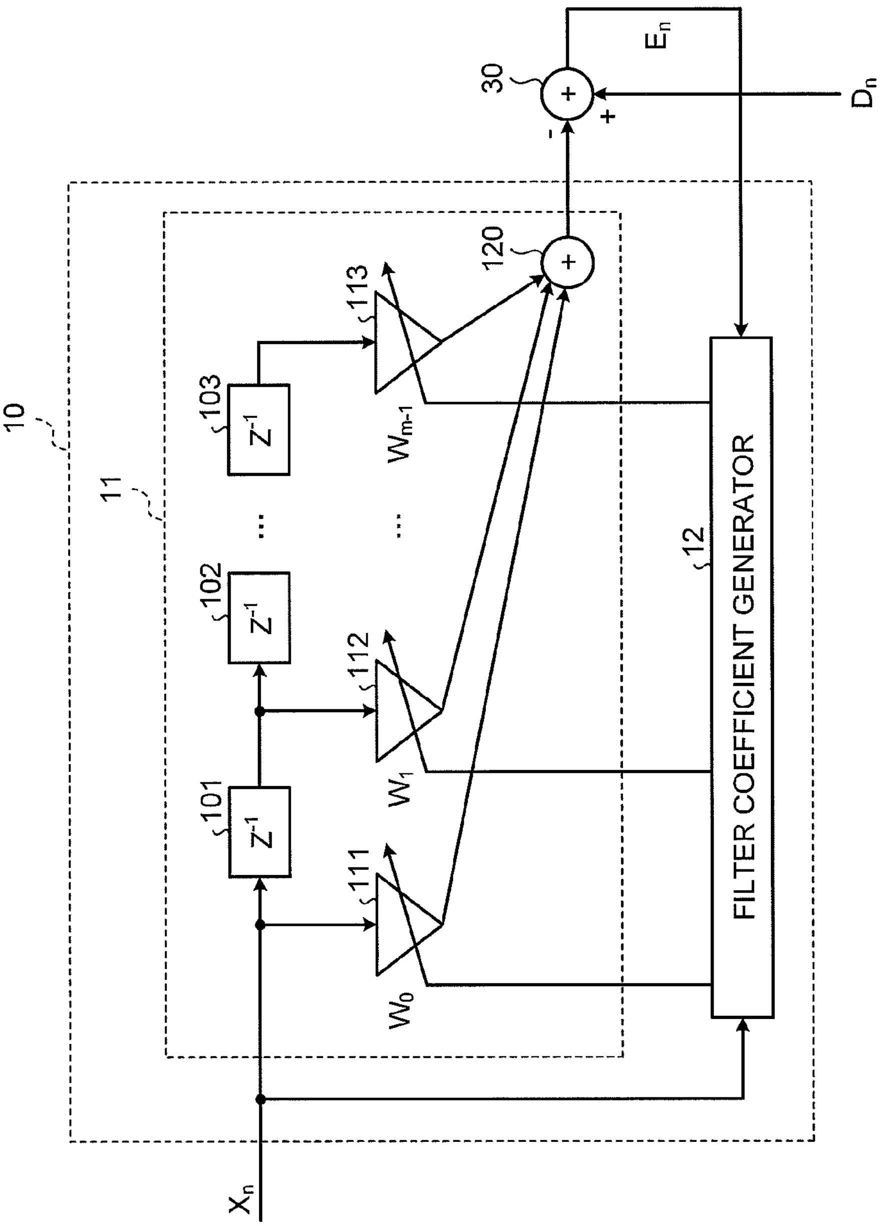
FIG. 8 is a circuit block diagram of an adaptive filter in a conventional example.

Alternatively, the output signals are converted from digital to analog and are output to a speaker or the like. In this embodiment, the adaptive filter 10 and the subtracter 30, similar to the conventional example illustrated in FIG. 8, are configured to use the variable filter 11. The filter coefficient generator 12 adjusts filter coefficients $W_0, W_1, \ldots, W_{m-1}$ by using the LMS algorithm. Here, m is a positive integer and, for example, is 101.

The variable filters 61 and 62 are FIR filters each having the same configuration as that of the variable filter 11. When the filter coefficients of the variable filter 61 are $W_0', W_1', \ldots, W_{m-1}'$, and the filter coefficients of the variable filter 62 are $W_0'', W_1'', \ldots, W_{m-1}''$, the filter coefficients are changed in accordance with changes in the filter coefficients $W_0, W_1, \ldots, W_{m-1}$ such that $W_0'=W_0''=W_0$, $W_1'=W_1''=W_1, \ldots$, and $W_{m-1}'=W_{m-1}''=W_{m-1}$.

An audio signal that is a recording target is assumed to have a frequency distribution of several tens Hz to 20 KHz. Among this, while frequency components of zero to several KHz are almost the same as those of the signals of the left and right channels Lch and Rch, frequency components of higher frequencies are different from those of the signals of the left and right channels Lch and Rch due to stereo components depending on the direction of a sound source. This frequency depends on the distance of the two microphones that are arranged.

On the other hand, a wind noise mixed into each microphone has a frequency component distribution of up to 1 KHz at most. The upper limit of the passband of the LPFs 41 and 42 is near 1 KHz. Thus, by subtracting the signal of the right channel Rch, which has passed through the LPF 42, from the signal of the left channel Lch, which has passed through the LPF 41, a signal is formed which has no component of an audio signal, which is a recording target, and is configured only by the wind noise. The reason for this is that there is no correlation between wind noises mixed into the two microphones, and by subtracting the signal of the right channel Rch from the signal of the left channel Lch, a value of zero is not acquired.

Alternatively, the signal of the left channel Lch may be subtracted from the signal of the right channel Rch. In addition, instead of the LPF, a band pass filter (BPF) may be used. The lower limit of the passband of the BPF is set to several tens Hz, and the upper limit thereof is set to 1 KHz. Since a frequency component of a several tens Hz or less is small in the wind noise, the influence of noises due to the other factors can be excluded.

In addition, alternatively, the same effect can be acquired by performing subtraction of the signals of the left and right channels Lch and Rch from each other using the subtracter 71 and applying the LPF or the BPF to a resultant signal. Alternatively, the LPF may not be arranged. Since a difference due to stereo components is smaller than the wind noise, the influence on a final result is not large even in a case where the LPF (or the BPF) is not applied.

As a signal generated by the signal generator 74, a sinusoidal wave of 1 KHz or a sum of a sinusoidal wave of 1 KHz and a sinusoidal wave of 2 KHz is used. The generated signal is input also to the delay unit 75. The input signal is delayed by the delay unit 75 and is input to the subtracter 30 as a desired signal. The amount of the delay of the delay unit 75 is set to be the same as the group delay of the variable filter 11.

Accordingly, the input signal that is input to the adaptive filter 10 is the generated signal+the wind noise, and the desired signal is a signal acquired by delaying the generated signal. The filter coefficients of the variable filter 11 are adjusted such that the output of the adaptive filter 10 and an error signal of the desired signal are zero. In other words, the filter coefficients are adjusted such that, even when the wind noise momentarily changes, the wind noise is eliminated in accordance with the change.

The variable filters 61 and 62 change the filter coefficients thereof together with the filter coefficients of the variable filter 11 and thus, similarly, have characteristics of eliminating a wind noise in accordance with the wind noise that momentarily changes.

Each one of the delay units 51 and 52 has almost the same amount of delay as the group delay of the LPFs 41 and 42. However, the amount of delay thereof may be larger than the group delay of the LPFs 41 and 42. The response of the adaptive filter 10 follows a change in the wind noise with a slight delay, and accordingly, by increasing the amount of delay corresponding to the delay, the performance of elimination of the wind noise at the time of the start thereof is improved. The delay units 51 and 52 may not be arranged. In such a case, while the performance of elimination of the wind noise at the time of the start thereof is degraded, there are advantages from the aspects of the amount of calculation and the scale of the circuit.

Here, while the generated signal is described to be delayed by the delay unit 75, a process that is equivalent thereto may be performed. The generated signal is a sinusoidal wave of 1 KHz or a sum of a sinusoidal wave of 1 KHz and a sinusoidal wave of 2 KHz; and a signal acquired by delaying the signal by a predetermined time is a signal of a sinusoidal wave of which the phase is shifted by an amount corresponding to the delay, or a signal acquired by adding sinusoidal waves of which the phase is shifted by an amount corresponding to the delay. Accordingly, such a signal may be calculated through an operation.

Alternatively, it may be configured such that waveform data of such a signal is stored in a memory in advance, and the waveform data is read out with the read-out start address being changed by the amount corresponding to the phase as the output data of the signal generator 74 and the delay unit 75.

In this embodiment, an example of a case in which there are two microphones of signals of the left and right channels Lch and Rch has been illustrated, but three or more microphones may be similarly configured. In the case of three microphones, the signal of the third microphone is processed by a delay unit that is similar to the delay unit 51 and a variable filter that is similar to the variable filter 61. The signals of two microphones are processed in a way similar to that illustrated in FIG. 1.

In addition, while the variable filters 11, 61, and 62 are configured by FIR filters and the adaptation process is performed using the LMS algorithm, instead of the LMS algorithm, an RLS algorithm or the like may be used. Furthermore, instead of the FIR filter, an IIR filter may be used.

Alternatively, it may be configured such that a transform into the frequency domain is performed using an orthogonal transform, and an adaptation process of the weighting factor of the frequency component thereof is performed.

In addition, while the signal has been described to be multiplied by ½ by the constant multiplier 72, a constant other than ½ may be used.

In the description presented above, although the number of filter taps and the filter coefficients of each one of the variable filters 61 and 62 are configured to be same as those of the variable filter 11 disposed inside the adaptive filter 10, the numbers of filter taps and the filter coefficients may not be the same. In such a case, it can well be addressed by changing the characteristics of the variable filters 61 and 62 in accordance with a change in the characteristics of the variable filter 11. As will be described in third embodiment, in a case where the sampling frequency of the input signal of the adaptive filter is decreased, the numbers of filter taps and the filter coefficients that are not the same are used, and the filter coefficients of the variable filters 61 and 62 are changed in accordance with a change in the filter coefficients of the variable filter 11.

In addition, in the description presented above, although the signal generated by the signal generator 74 is presented to be a sinusoidal wave of 1 KHz or a sum of a sinusoidal wave of 1 KHz and a sinusoidal wave of 2 KHz, other frequencies may be used, and the signal may be a sum of three or more sinusoidal waves.

Furthermore, in the description presented above, although the signal generated by the signal generator 74 is configured to be used, instead of such a signal that is internally generated, an arbitrary signal input from the outside may be used.

According to this embodiment, the wind noise can be adaptably suppressed in accordance with the magnitude or the frequency distribution of the wind noise.

Second Embodiment

Figure 2:
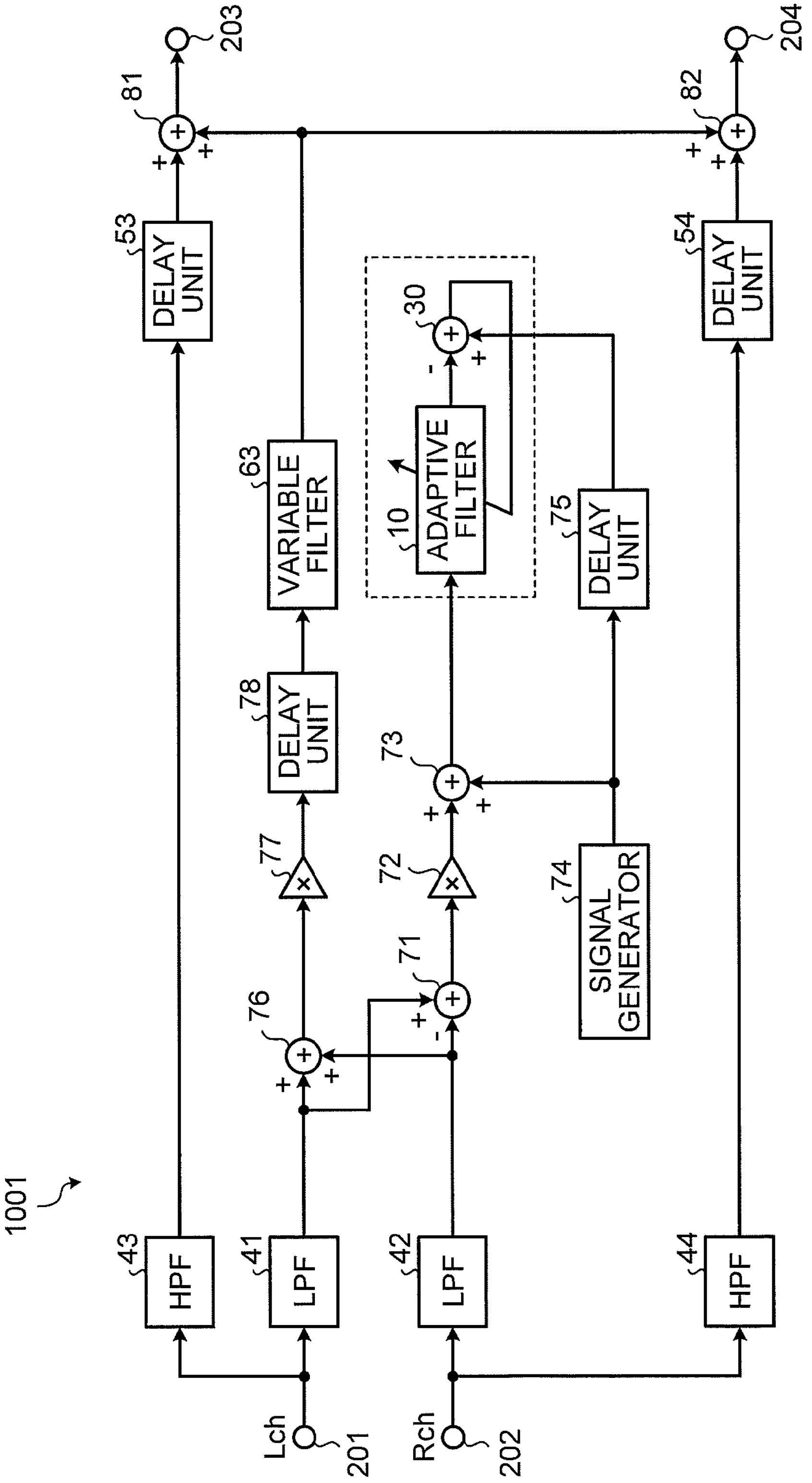
FIG. 2 is a configuration diagram of a noise eliminating device according to a second embodiment.

A noise eliminating device according to this embodiment will be described with reference to FIG. 2. FIG. 2 is a diagram that illustrates the configuration of the noise eliminating device. A noise eliminating device 1001 according to this embodiment, similar to the first embodiment, performs a noise eliminating process for audio signals received from microphones arranged inside a casing of an electronic apparatus. In other words, audio signals of right and left channels Rch and Lch of stereo transmitted from two microphones are converted from analog to digital; and the converted signals are input from input terminals 201 and 202. Here, description of processes that are the same as those of first embodiment will not be presented as is appropriate.

Similar to First embodiment illustrated in FIG. 1, the noise eliminating device 1001 is equipped with: an adaptive filter 10; a subtracter 30; an LPF 41; an LPF 42; a subtracter 71; a constant multiplier 72; an adder 73; a signal generator 74; a delay unit 75; input terminals 201 and 202; and output terminals 203 and 204; an adder 76; a constant multiplier 77; a delay unit 78; a variable filter 63; a high pass filter (HPF) 43; an HPF 44; delay units 53 and 54; and adders 81 and 82.

The noise eliminating device 1001 may be realized by an analog circuit, a digital circuit, and the like, by software of a central processing unit (CPU), a digital signal processor (DSP), or the like, or by a combination thereof.

The audio signal of the left channel Lch input to the input terminal 201 is input to the LPF 41 and the HPF 43. The audio signal of the right channel Rch input to the input terminal 202 is input to the LPF 42 and the HPF 44. The characteristics of the HPF and the LPF are configured to be complementary by allowing the cut-off frequencies thereof to coincide with each other, whereby bandwidth division is performed. Similar to First embodiment, the outputs of the LPFs 41 and 42 are input to the subtracter 71. The operations of the constant multiplier 72, the adder 73, the adaptive filter 10, the subtracter 30, the signal generator 74, and the delay unit 75 are the same as those of First embodiment.

In addition, the outputs of the LPFs 41 and 42 are input to the adder 76. The adder 76 calculates a sum signal of the audio signals of the left and right channels Lch and Rch. The subtracter 71 and the adder 76 serve as a signal calculator that calculates a difference signal and a sum signal of the signal of one channel and the signal of the other channel.

The sum signal is multiplied by ½ by the constant multiplier 77 and then is input to the delay unit 78. The output of the delay unit 78 is input to the variable filter 63. The variable filter 63 has the same configuration as the variable filters 61 and 62 illustrated in FIG. 1 and performs the same operation as that thereof. In other words, when the filter coefficients of the variable filter 63 are $W_0'''$, $W_1'''$, . . . , $W_{m-1}'''$, the filter coefficients are changed in accordance with changes in the filter coefficients $W_0$, $W_1$, . . . , $W_{m-1}$ such that $W_0'''=W_0$, $W_1'''=W_1$, . . . , and $W_{m-1}'''=W_{m-1}$.

The delay unit 78 delays the signal such that the response of the adaptive filter 10 follows a change in the wind noise with a slight delay.

The delay unit 78 has an amount of delay that corresponds to the delay. The delay unit 78 may not be arranged. In such a case, while the performance of elimination of the wind noise at the time of the start thereof is degraded, there are advantages from the aspects of the amount of calculation and the scale of the circuit.

The output of the variable filter 63 is one input of each one of the adders 81 and 82. A signal acquired by delaying the output of the HPF 43 using the delay unit 53 is input to the other input of the adder 81. In addition, a signal acquired by delaying the output of the HPF 44 using the delay unit 54 is input to the other input of the adder 82. The amount of delay of the delay unit 53 is set such that a sum of the group delay of the LPF 41, the delay of the delay unit 78, and the group delay of the variable filter 63 is the same as a sum of the group delay of the HPF 43 and the delay of the delay unit 53. This applies the same to the delay unit 54. The outputs of the adders 81 and 82 are output respectively from the output terminals 203 and 204.

As described above, while the band of the noise is at most up to 1 KHz, audio signals as recording targets have a difference due to stereo components in a band that is several KHz or more. Thus, the bandwidth division is performed with the cutoff of the LPFs 41 and 42 and the HPFs 43 and 44 set to be near 1 KHz. As a result, the influence of the wind noise is not present in the outputs of the HPFs 43 and 44.

The outputs of the LPFs 41 and 42 are signals mixed audio signals that are approximately the same in the left and right channels Lch and Rch and wind noises that have no correlation between the left and right channels Lch and Rch. The output of the subtracter 71, as described in first embodiment, corresponds to the wind noise only.

In addition, the sum signal that is the output of the adder 76 and the constant multiplier 77 has an improved wind noise ratio (SNR) with respect to the audio signal as the recording target, compared to the only signal of the left channel Lch or the right channel Rch. The reason for this is that there is a correlation between the audio signals; and there is no correlation between the wind noises. Accordingly, the SNR of the output signals of the output terminals 203 and 204, which is final output, is improved. Alternatively, a configuration may be employed in which, instead of the sum signal, the output of the LPF 41 or the LPF 42 is directly input to the delay unit 78. In such a case, while there is a disadvantage in terms of the SNR, there is an advantage of reducing the amount of calculation.

As described above, the filter coefficients of the variable filter 63 are changed in accordance with changes in the filter coefficients of the variable filter 11. As described in first embodiment, the adaptive filter 10 operates to reduce a wind noise that momentarily changes; and accordingly, the variable filter 63 also reduces the wind noise included in the sum signal.

The output of the variable filter 63 is one input of each one of the adders 81 and 82. The other inputs thereof are higher-band signals, which have been delayed, acquired through bandwidth division. Thus, by adding the input signals using the adders 81 and 82, signals of the entire band are acquired.

Similar to first embodiment, the LPFs 41 and 42 may be substituted by BPFs. Here, although the difference signal and the sum signal are calculated after the LPFs 41 and 42 are applied, it may be configured such that the difference signal and the sum signal are calculated first, and LPFs are applied respectively to the results thereof.

As above, according to this embodiment, by performing bandwidth division, wind noise reduction is performed only for a signal of the low band having a small difference due to a stereo component and having a high influence of the wind noise thereon using the variable filter, but no process is performed for a higher band signal having a low influence of the wind noise thereon; whereby the wind noise can be reduced without degrading the audio signal that is a recording target. In addition, compared to first embodiment, the number of variable filters each having a relatively large amount of calculation can be a half of that of first embodiment. By decreasing the amount of calculation, the power consumption decreases. In addition, by configuring the low band signal as the sum signal, the wind noise can be further reduced.

Third Embodiment

Figure 3:
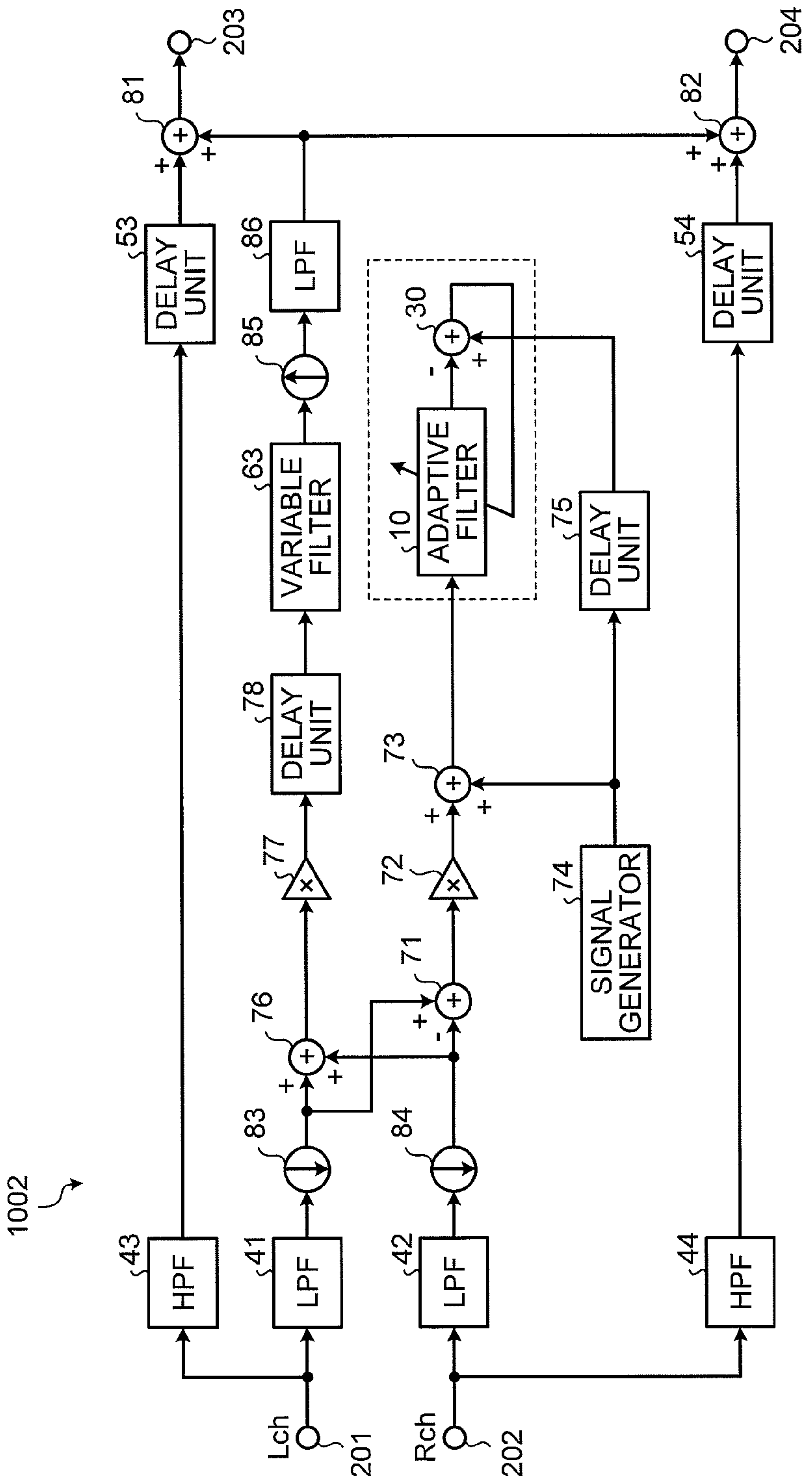
FIG. 3 is a configuration diagram of a noise eliminating device according to a third embodiment.

A noise eliminating device according to this embodiment will be described with reference to FIG. 3. FIG. 3 is a diagram that illustrates the configuration of the noise eliminating device. A noise eliminating device 1002 according to this embodiment, similar to second embodiment, performs a noise eliminating process for audio signals received from microphones arranged inside a casing of an electronic apparatus. In other words, audio signals of right and left channels Rch and Lch of stereo transmitted from two microphones are converted from analog to digital, and the converted signals are input from input terminals 201 and 202. Here, description of processes that are the same as those of second embodiment will not be presented as is appropriate.

According to this embodiment, decimeters 83 and 84 and an interpolator 85 are added to the configuration of second embodiment.

The decimeter 83 thins out a half of the output data of the LPF 41. A signal that is input from an input terminal 201 is digital data having a sampling frequency Fs. As the output of the decimeter 83, data is thinned out by half to be digital data having a sampling frequency of Fs/2.

Similarly, the decimeter 84 thins out a half of the output data of the LPF 42.

Instead of thinning out the data by using the decimeters 83 and 84, the operations of the LPFs 41 and 42 may be operated in a half thinning-out pattern so as to configure the sampling frequency of the output data to be Fs/2.

A subtracter 71, a constant multiplier 72, an adder 73, an adaptive filter 10, a subtracter 30, a signal generator 74, a delay unit 75, an adder 76, a constant multiplier 77, a delay unit 78, and a variable filter 63 operate at the sampling frequency Fs/2.

The output of the variable filter 63 is converted into digital data having the original sampling frequency Fs by using the interpolator 85 and the LPF 86. More specifically, the sampling frequency is increased by inserting data "0" by the interpolator 85 at sampling points that have been thinned out by using the decimeter; and the LPF 86 that is an interpolation filter is further applied thereto.

As is known from the Nyquist sampling theorem, the sampling frequency needs to be twice the signal band or more. Since the outputs of the LPFs 41 and 42 have a limited signal band due to a low pass characteristic, the sampling frequency can be lowered. Accordingly, the degree of the thinning-out may be increased like Fs/3 or Fs/4 depending on a band limit value of the sampling frequency Fs according to the LPF.

According to this embodiment, the frequency in which the adaptive filter operation or the variable filter operation is performed can decrease. The adaptive filter operation and the variable filter operation need to be performed for every sampling cycle of the input data, and accordingly, the amount of the operations increases in a case where the sampling frequency is high. Since this amount of the operations can decrease, the power consumption can be reduced.

In the configuration illustrated in FIG. 3, although the data is represented to be input to the adder 76 and the subtracter 71 after the sampling frequencies are lowered by the decimeters 83 and 84, the thinning-out process may be performed in a subsequent stage of the adder 76 and the subtracter 71. In such a case, the thinning-out process may not be performed on the output side of the adder. In a case where the thinning-out process is not performed on the output side of the adder, the processes of the interpolator 85 and the LPF 86 are not performed as well. In such a case, the adaptive filter 10 and the variable filter 63 operate at mutually-different sampling frequencies, and accordingly, the coefficients of the adaptive filter are changed so as to be used by the variable filter. For example, for the m-th order of the number of taps of the variable filter 11 disposed inside the adaptive filter, the number of taps of the variable filter 63 is set to "2×m−1". For example, for m=3rd order, the number of taps of the variable filter is the 5th order.

When the filter coefficients of the variable filter 63 are $V_0$, $V_1, \ldots, V_4$, and the filter coefficients of the variable filter 11 are $W_0$, $W_1$, and $W_2$, it is set such that $V_0=K\times W_0$, $V_2=K\times W_1$, and $V_4=K\times W_2$, filter coefficients $V_1$ and V3 are calculated by applying an interpolation filter to a data row $V_0$, 0, $V_0$, 0, and $V_2$ in which the filter coefficients are set as "0". Here, K is a constant used for adjusting filter gains.

In addition, also in the noise eliminating device 1000 according to the first embodiment, it may be configured such that a decimation process is performed for the outputs of the LPFs 41 and 42, and the sampling frequency is lowered to perform the process of the adaptive filter 10 or the like. Also in such a case, since the variable filters 61 and 62 operate at the original sampling frequency, the coefficients of the adaptive filter are converted and used.

Forth Embodiment

Figure 4:
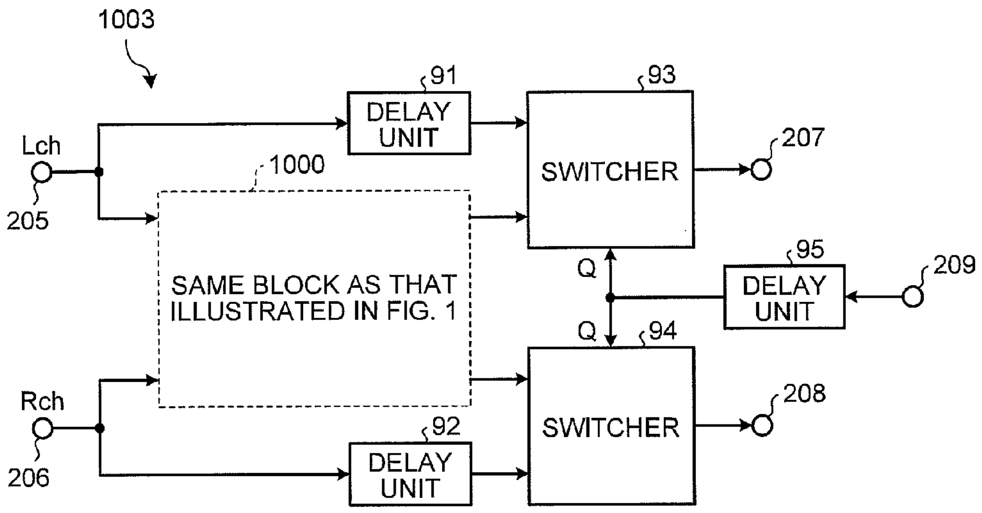
FIG. 4 is a configuration diagram of a noise eliminating device according to a fourth embodiment.

A noise eliminating device according to this embodiment will be described with reference to FIG. 4. FIG. 4 is a diagram that illustrates the configuration of the noise eliminating device. A noise eliminating device 1003 according to this embodiment, similar to the first to third embodiments, performs a noise eliminating process for audio signals received from microphones arranged inside a casing of an electronic apparatus. In other words, audio signals of right and left channels Rch and Lch of stereo transmitted from two microphones are converted from analog to digital, and the converted signals are input from input terminals 205 and 206. Here, description of processes that are the same as those of first embodiment will not be presented as is appropriate.

In this embodiment, a configuration is employed in which the noise eliminating device 1000 according to first embodiment illustrated in FIG. 1 is internally included; and the output thereof and audio signals of the left and right channels Lch and Rch are switched and output.

Figure 5:
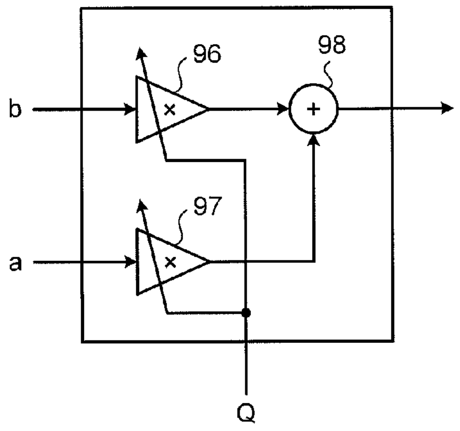
FIG. 5 is a diagram that illustrates a switching unit of the noise eliminating device according to the fourth embodiment.

The audio signal of the left channel Lch input to the input terminal 205 is input to an input terminal 201 of the noise eliminating device 1000 and is input to a delay unit 91. The output of the delay unit 91 is input to a switcher 93. A signal transmitted from an output terminal 203 of the noise eliminating device 1000 is also input to the switcher 93. In addition, a signal transmitted from a control input terminal 209 is delayed by a delay unit 95 and is input to the Q input of the switcher 93. The internal configuration of the switcher 93 is illustrated in FIG. 5. The switcher 93 includes multipliers 96 and 97 and an adder 98 and outputs Q×a+(1−Q)×b for input signals a and b and a control signal Q (0≤Q≤1).

The output of the switcher 93 is output from an output terminal 207 as a signal of the left channel Lch from which a wind noise is reduced. Similarly, an audio signal of the right channel Rch input to the input terminal 206 is input to an input terminal 202 of the noise eliminating device 1000 and is input to a delay unit 92. The output of the delay unit 92 and a signal transmitted from the output terminal 204 of the noise eliminating device 1000 are input to a switcher 94. Such signals are switched by the switcher 94 and are output from an output terminal 208. The internal configuration of the switcher 94 is as illustrated in FIG. 5.

The delay units 91 and 92 have the same amount of delay as that of the signal delay of the noise eliminating device 1000.

In a case where this embodiment is used in a voice recording unit of a mobile device, a wind may not blow all the time and may not flow for a long time. In such a case, it is not desirable to continuously operate the noise eliminating device 1000 from the viewpoint of power consumption. Thus, the noise eliminating device 1000 is appropriately operated by using a control signal transmitted from the control input terminal 209.

Figure 6:
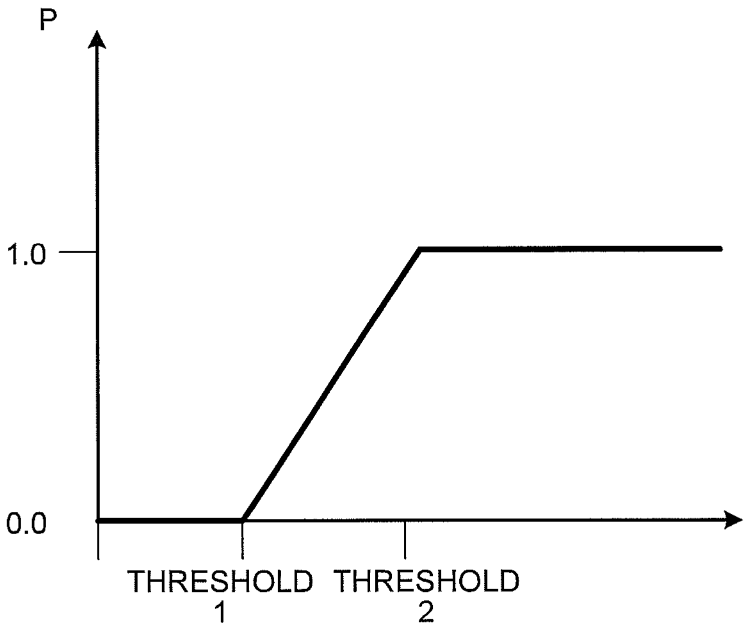
FIG. 6 is a graph that illustrates a threshold used for switching the switching unit.

An input signal P that is input to the control input terminal 209, for example, is calculated by using a wind pressure sensor disclosed in Japanese Patent Laid-open Publication H5-328480 A. Alternatively, by allowing a difference signal between the audio signals of the left and right channels Lch and Rch to pass through a BPF, the input signal may be calculated based on data acquired by performing peak detection of the absolute value of the output thereof. Here, the passband of the BPF is set to 100 Hz to 1 KHz or the like corresponding to a major component of the wind. The control signal P is generated to have characteristics as represented in FIG. 6 for the output of the pressure sensor or the output of the BPF. In FIG. 6, the horizontal axis represents the air flow amount, and the vertical axis represents the magnitude of the control signal P.

When the input signal P that is input to the control input terminal 209 is zero, the internal circuit of the noise eliminating device 1000 is not operated; and the LPFs, the adaptive filter, the variable filter, and the delay units disposed therein are in the initial states. In other words, since there are registers for maintaining data and memories used for the filter coefficients in such circuits, the values of the registers are set to zero, and the values of the memories used for the filter coefficients are set to initial values thereof.

When the wind starts to blow, and the input signal P is non-zero, the operation of the circuits of the noise eliminating device 1000 is started. Here, a certain time is required for the adaptive filter to converge at the characteristics corresponding to the input signal. The delay unit 95 compensates for this time; and delays the P signal by a predetermined time and supplies the delayed signal to the Q input of the switchers 93 and 94.

In addition, in a case where the wind stops from a wind blowing state, after the output of the delay unit 95 becomes zero, the operation of the circuits of the noise eliminating device 1000 is stopped.

According to this embodiment, in a case where the wind does not blow, the power consumption can be reduced.

In this embodiment, although the noise eliminating device 1000 is used as the internal circuit, any one of the noise eliminating devices 1001 and 1002 may be used.

Fifth Embodiment

Figure 9:
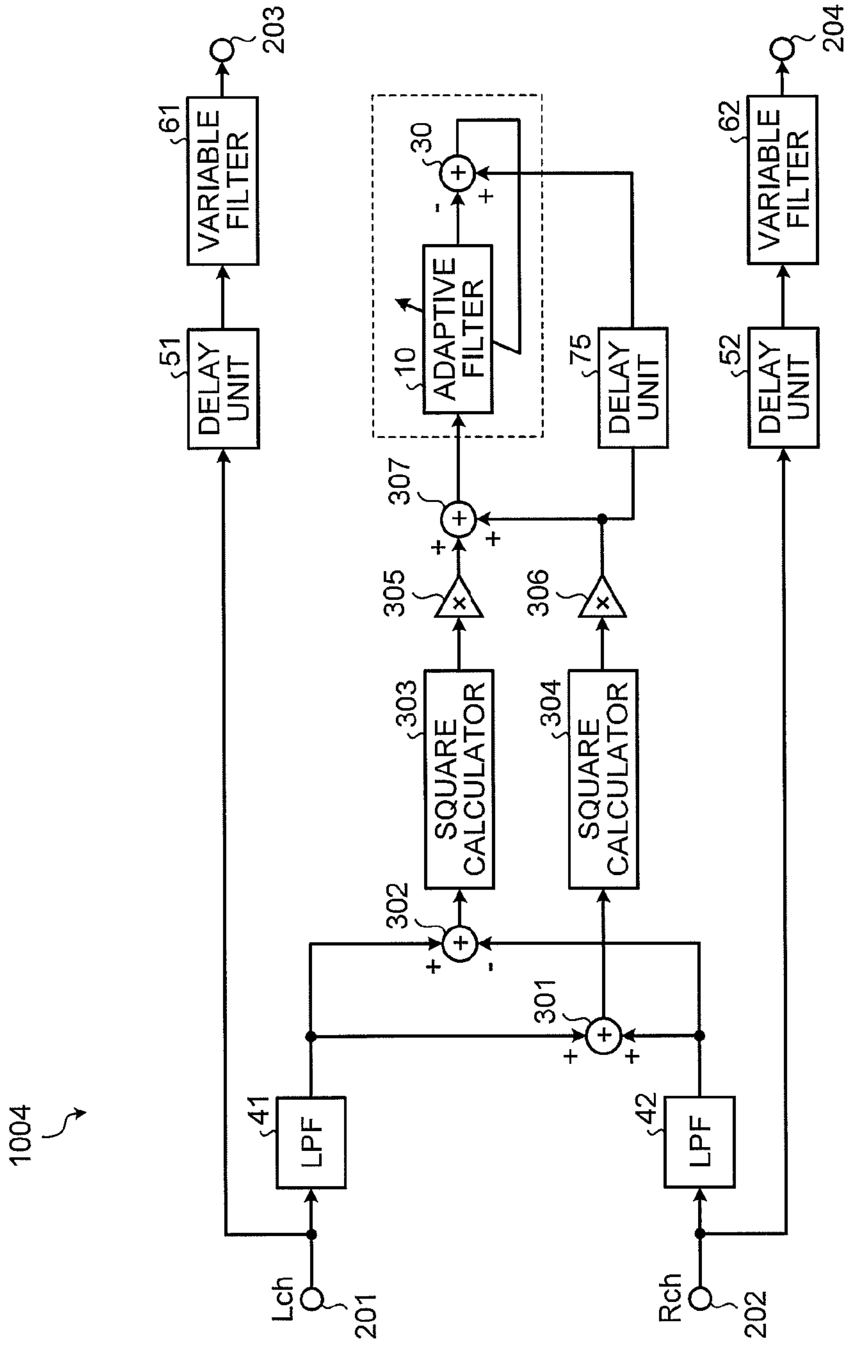
FIG. 9 is a configuration diagram of a noise eliminating device according to a fifth embodiment.

A noise eliminating device according to this embodiment will be described with reference to FIG. 9. FIG. 9 is a diagram that illustrates the configuration of the noise eliminating device. In the noise eliminating device 1004 according to this embodiment, a part of the noise eliminating device 1000 according to the first embodiment is replaced. Here, description of processes that are the same as those of the first embodiment will not be presented as is appropriate.

Similar to first embodiment illustrated in FIG. 1, the noise eliminating device 1004 is equipped with: an adaptive filter 10; a subtracter 30; a delay unit 75; an LPF 41; an LPF 42; delay units 51 and 52; variable filters 61 and 62; input terminals 201 and 202; and output terminals 203 and 204; an adder 301; a subtracter 302; square calculators 303 and 304; constant multipliers 305 and 306; and an adder 307. The noise eliminating device 1004 may be realized by an analog circuit, a digital circuit, and the like, software of a central processing unit (CPU), a digital signal processor (DSP), or the like, or a combination thereof.

The outputs of the LPFs 41 and 42 are input to the adder 301 and the subtracter 302. The adder 301 calculates a sum signal of audio signals of the left and right channels Lch and Rch; and the subtracter 302 calculates a difference signal between the audio signals of the left and right channels Lch and Rch. The subtracter 302 and the adder 301 serve as a signal calculator that calculates a difference signal and a sum signal of the signals of one channel and the other channel.

The difference signal is input to the square calculator 303. The square calculator 303 calculates the square of the input signal and outputs a resultant signal. In other words, when the input signal data row is $S_K$, $S_{K+1}$, $S_{K+2}$, . . . , the output signal data row is $S_K^2$, $S_{K+1}^2$, $S_{K+2}^2$, . . . . Similarly, the sum signal is input to the square calculator 304, and the square of the input is calculated and output. The square calculators 303 and 304 respectively serve as first and second non-linear processing units. The output of the square calculator 303 is multiplied by ¼ by the constant multiplier 305 and then is input to the adder 307. The output of the square calculator 304 is multiplied by ¼ by the constant multiplier 306 and then is input to the other input of the adder 307. The output of the adder 307 is the input of the adaptive filter 10. The output of the adder 307 is a composite signal of the outputs of the first and second non-linear processing unit.

The output of the constant multiplier 306 is input also to the delay unit 75. The output of the delay unit 75 is input to the subtracter 30 as a desired signal of the adaptive filter. The output of the delay unit 75 is a signal acquired by delaying the output signal of the second non-linear processing unit.

Although a wind noise is mixed to an audio signal as a recording target in the output signal of the adder 301, the audio signal is a major signal. On the other hand, a wind noise is a major component of a signal in the output signal of the subtracter 302. As a desired signal of the adaptive filter, a signal is delayed and used which is acquired by calculating the square of the output of the adder 301 in which the audio signal is major. In addition, the output of the adder 307 is the input of the adaptive filer and is a sum of a signal that is acquired by calculating the square of the output of the adder 301, in which the audio signal is major, and multiplying the result by a constant and a signal acquired by calculating the square of the output of the subtracter 302, in which the wind noise is major, and multiplying the result by a constant. In other words, the adaptive filter 10 is operated in a state in which a signal in which a wind noise component is mixed to an audio signal component is set as an input signal, and a signal in which the audio signal component is major is set as a desired signal. Accordingly, characteristics in which only the wind noise component is suppressed are acquired. Since the characteristics are the characteristics of the variable filters 61 and 62, the variable filters 61 and 62 can suppress only the wind noise component from an input signal in which the wind noise is mixed in the audio signal as a recording target. Here, although the signals are represented to be multiplied by ¼ by the constant multipliers 305 and 306, a constant other than ¼ may be used, and mutually-difference constants may be respectively used for the constant multipliers 305 and 306.

In addition, as the input of the square calculator 304, not the output of the adder 301 but either the output of the LPF 41 or the output of the LPF 42 may be input. In the output signals of the LPFs 41 and 42, audio signals that are recoding targets are major signals.

In this embodiment, although the square calculators are used as the first and second non-linear processing units, absolute value implementing units may be used. The absolute value implementing unit calculates the absolute value of an input signal and outputs the calculated result. In other words, when the input signal data row is $S_k$, $S_{k+1}$, $S_{k+2}$, . . . , the output signal data row is $|S_k|$, $|S_{k+1}|$, $|S_{k+2}|$, . . . .

In addition, modified examples described in first embodiment may be similarly used in this embodiment.

However, the delay unit 75 cannot be substituted with the calculation through an operation. According to this embodiment, for a wind noise, only a noise component can be adaptively suppressed in accordance with the magnitude or the frequency distribution of the wind noise.

Sixth Embodiment

Figure 10:
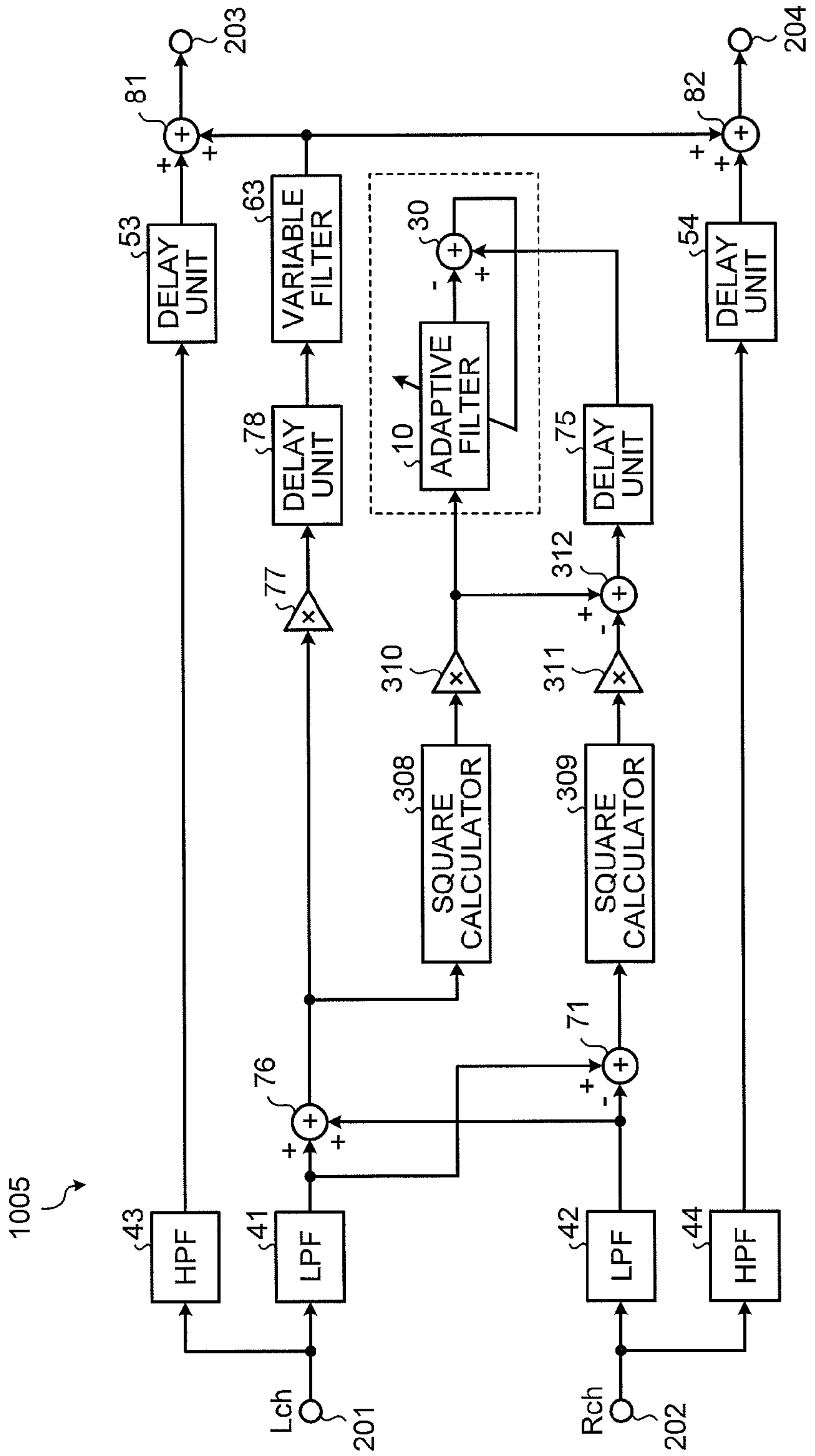
FIG. 10 is a configuration diagram of a noise eliminating device according to a sixth embodiment.

A noise eliminating device according to this embodiment will be described with reference to FIG. 10. FIG. 10 is a diagram that illustrates the configuration of the noise eliminating device. In the noise eliminating device 1005 according to this embodiment, a part of the noise eliminating device 1001 according to second embodiment is replaced. Here, description of processes that are the same as those of second embodiment will not be presented as is appropriate.

Similar to second embodiment illustrated in FIG. 2, the noise eliminating device 1005 is equipped with: an adaptive filter 10; a subtracter 30; an LPF 41; an LPF 42; a subtracter 71; a delay unit 75; input terminals 201 and 202; output terminals 203 and 204; an adder 76; a constant multiplier 77; a delay unit 78; a variable filter 63; a high pass filter (HPF) 43; an HPF 44; delay units 53 and 54; adders 81 and 82; square calculators 308 and 309; constant multipliers 310 and 311; and a limited subtracter 312.

The noise eliminating device 1005 may be realized by an analog circuit, a digital circuit, and the like, software of a central processing unit (CPU), a digital signal processor (DSP), or the like, or a combination thereof.

The outputs of the LPFs 41 and 42 are input to the subtracters 71 and adder 76. The subtracter 71 calculates a difference signal between the audio signals of the left and right channels Lch and Rch. The adder 76 calculates a sum signal of the audio signals of the left and right channels Lch and Rch. The subtracter 71 and the adder 76 serve as a signal calculator that calculates a difference signal and a sum signal of the signal of one channel and the signal of the other channel.

The sum signal is multiplied by ½ by the constant multiplier 77 and then is input to the delay unit 78, as well as the sum signal being input to the square calculator 308. The square calculator 308, similar to the square calculator 303, calculates the square of an input signal and outputs a resultant signal. The square calculator 308 serves as a second non-linear processing unit. The output of the square calculator 308 is multiplied by ¼ by the constant multiplier 310 and is the input signal of the adaptive filter 10 as well as being input to the limited subtracter 312.

The difference signal is input to the square calculator 309. The square calculator 309, similar to the square calculator 303, calculates the square of the input signal and outputs a resultant signal. The square calculators 309 serve as a first non-linear processing unit. The output of the square calculator 309 is multiplied by ¼ by the constant multiplier 311 and is input to the limited subtracter 312.

The limited subtracter 312 outputs a result of the subtraction in a case where the output signal of the constant multiplier 310 is larger than the output signal of the constant multiplier 311; and outputs "0" in the other cases.

The output of the limited subtracter 312 is a composite signal of the output signal of the first non-linear processing unit and the output signal of the second non-linear processing unit. The output of the limited subtracter 312 is input to the delay unit 75. The output of the delay unit 75 is a delayed signal of a composite signal of the output signal of the first non-linear processing unit and the output signal of the second non-linear processing unit.

The output signal of the adder 76 is a signal of an audio signal mixed with a wind noise, the audio signal being a recording target. On the other hand, a wind noise is a major component of a signal in the output of the subtracter 71. In the limited subtracter 312, a signal, which is acquired by subtracting a signal that is acquired by calculating the square of the output of the subtracter 71 and multiplying a resultant signal by a constant from a signal that is acquired by calculating the square of the output of the adder 76 and multiplying a resultant signal by a constant, is a signal acquired by subtracting a wind noise component from an audio signal that is a recording target mixed with a wind noise; and accordingly, a signal of only the audio signal component of the recording target is acquired. In other words, the adaptive filter 10 is operated in a state in which a signal in which the wind noise component is mixed to an audio signal component is set as an input signal, and a signal in which the audio signal component is major is set as a desired signal. Accordingly, characteristics in which only the wind noise component is suppressed are acquired. Since the characteristics are the characteristics of the variable filter 63, the variable filter 63 can suppress only the wind noise component from an input signal in which the wind noise is mixed in the audio signal as a recording target.

Here, although the signals are represented to be multiplied by ¼ by the constant multipliers 310 and 311, a constant other than ¼ may be used, and mutually-difference constants may be respectively used for the constant multipliers 310 and 311.

In addition, as the input of the square calculator 308, not the output of the adder 76 but either the output of the LPF 41 or the output of the LPF 42 may be input. In the output signals of the LPFs 41 and 42, audio signals that are recoding targets are major signals. In the noise eliminating device 1006 illustrated in FIG. 11, the output of the LPF 41 is configured as the input of the square calculator 308. In the noise eliminating device 1006, the signal is multiplied by one by the constant multiplier 310. The other processes are the same as those of the noise eliminating device 1005, and thus, the description thereof will not be presented.

In this embodiment, although the square calculators are used as the first and second non-linear processing units, absolute value implementing units may be used. The absolute value implementing unit calculates the absolute value of an input signal and outputs the calculated result. In other words, when the input signal data row is $|S_k|$, $|S_{k+1}|$, $S_{k+2}$, . . . , the output signal data row is $|S_k|$, $|S_{k+1}|$, $|S_{k+2}|$, . . . .

In addition, modified examples described in second embodiment may be similarly used in this embodiment. However, the delay unit 75 cannot be substituted with the calculation through an operation.

Figure 11:
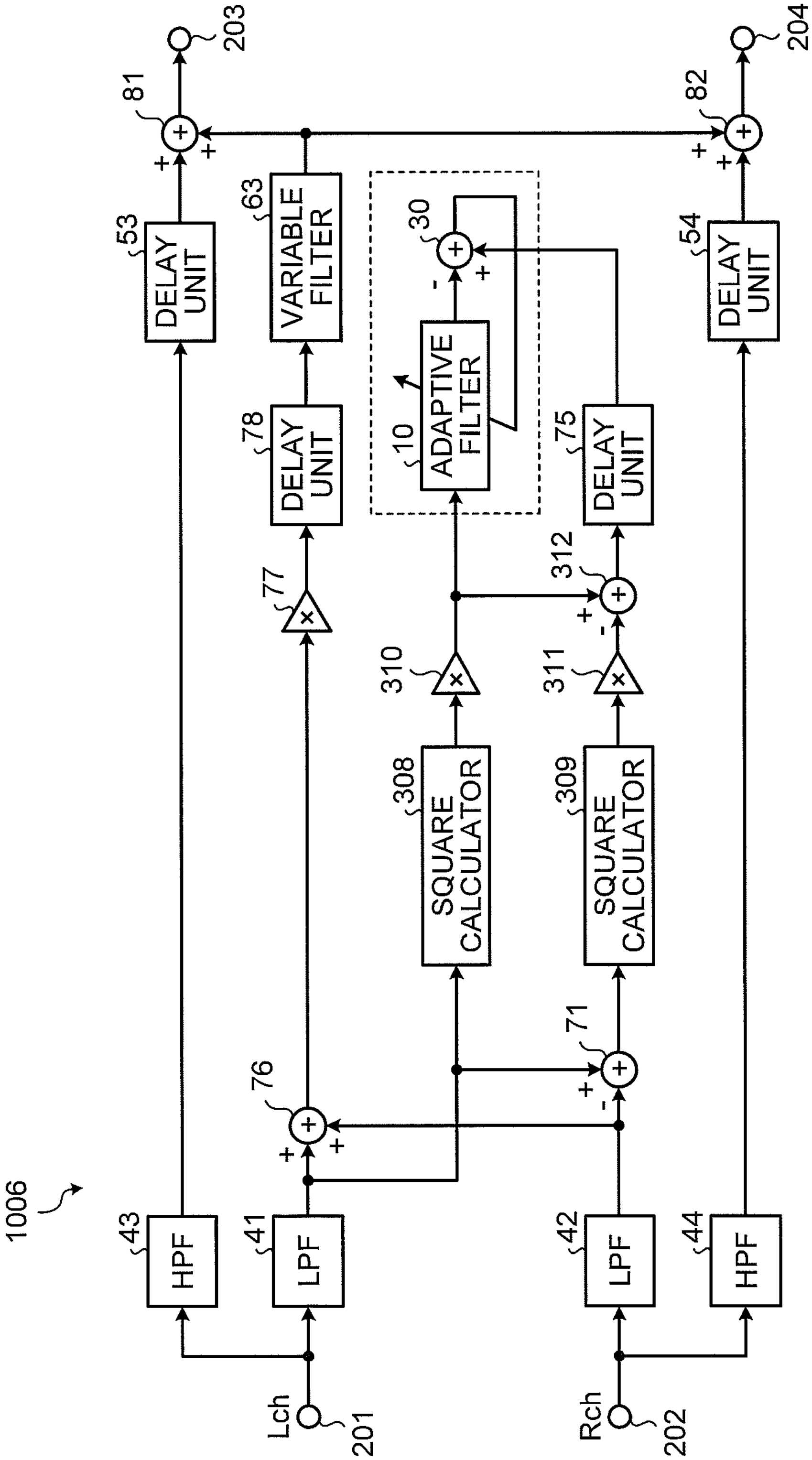
FIG. 11 is a configuration diagram of a noise eliminating device according to the sixth embodiment.

In addition, the parts of the noise eliminating device 1005 illustrated in FIG. 10 and the noise eliminating device 1006 illustrated in FIG. 11 that are configured by the square calculators 308 and 309, the constant multipliers 310 and 311, and the limited subtracter 312 may be substituted with the part of the noise eliminating device 1004 illustrated in FIG. 9 that is configured by the square calculators 303 and 304, the constant multipliers 305 and 306, and the adder 307. In such a case, the output of the subtracter 71 is input to the square calculator 303, and the output of the adder 76 or the output of the LPF 41 is configured to be the input of the square calculator 304.

In addition, the part of the noise eliminating device 1004 illustrated in FIG. 9 that is configured by the square calculators 303 and 304, the constant multipliers 305 and 306, and the adder 307 described in fifth embodiment may be substituted with the part of the noise eliminating device 1005 illustrated in FIG. 10 that is configured by the square calculators 308 and 309, the constant multipliers 310 and 311, and the limited subtracter 312. In such a case, the output of the subtracter 302 is input to the square calculator 309, and the output of the adder 301 is input to the square calculator 308.

According to this embodiment, for a wind noise, only a wind noise component can be adaptively suppressed in accordance with the magnitude or the frequency distribution of the wind noise.

In addition, in the noise eliminating device 1002 which is illustrated in FIG. 3 according to third embodiment, for the noise eliminating device 1001 illustrated in FIG. 2, the process of decimating the outputs of the LPFs 41 and 42 is performed. Similarly, also in the noise eliminating device 1004 which is illustrated in FIG. 9 according to fifth embodiment, the noise eliminating device 1005 which is illustrated in FIG. 10 according to sixth embodiment, and the noise eliminating device 1006 illustrated in FIG. 11, the process of decimating the outputs of the LPFs 41 and 42 may be performed.

Furthermore, in the noise eliminating device 1003 which is illustrated in FIG. 4 according to fourth embodiment, the switchers 93 and 94 are configured to be arranged so as to reduce the power consumption in a case where any wind does not blow. As a dotted line portion illustrated in FIG. 4, the noise eliminating device 1000, 1001, 1002, 1004, 1005, or 1006 may be used.

Other Embodiments

In the second, third and sixth embodiments, the bandwidth division is performed using the HPF and the LPF. Although the cutoff frequency of each filter at the time of the bandwidth division has been described to be fixed, the cutoff frequency may be configured to be changed based on a result of the detection of the air flow. While the output of the variable filter 63 is a result of reduction of the wind noise in the sum signal, the output and the outputs of the HPFs of both channels Lch and Rch are composed and are output, and accordingly, the same signal is used in both channels Lch and Rch for the low band component. Thus, when the cutoff frequency is too high, stereo feeling is damaged. On the other hand, in a case where the air flow is high, there is a component of a wind noise up to a relatively high frequency band, and accordingly, the cutoff frequency is desired to be high. By changing the cutoff frequency in accordance with the air flow, both the improvement of the stereo feeling and the reduction of the wind noise can be achieved.

In addition, the microphones of the channels Lch and Rch may not be used, but microphone of a plurality of channels may be used. For example, two or more microphones that are arranged to be close to each other may be used. Furthermore, the noise of only one channel Rch or Lch may be configured to be eliminated. Furthermore, the noise may be eliminated from audio signals received by a microphone array in which microphones are arranged in an array pattern.

When a peripheral voice is recorded using a microphone mounted in a portable-type voice recording device, a noise (hereinafter, referred to as a wind noise) due to a wind or a touch sound (hereinafter, referred to as a touch noise) that is generated in accordance with a touch on the casing of the device or the like may cause a problem.

The wind noise is configured mainly by a frequency component of 1 KHz or less and thus, may be frequently reduced using a technique for eliminating a wind noise component of a low band frequency component. As one method, as is proposed in the previous application of Japanese Patent Application No. 2012-23013 applied by the applicants of the present application, there is a technique of reducing a wind noise by eliminating a low band frequency component of a difference signal between audio signals of the left and right channels Lch and Rch in the frequency domain as a wind noise component. On the other hand, the touch noise is an impulse-pattern noise and has a wide frequency band, and accordingly, it is difficult to reduce the touch noise by eliminating a specific band. Thus, a technique is used in which an impulse-pattern noise part is attenuated or completely blocked, and interpolation is performed for the blocked period using previous and next signals or the like (Japanese Patent Application Publication Laid-open 2005-303681 A). The techniques for reducing these two noises are effective for respective target noises. However, when such a technique is used for a non-target noise, no effect is achieved, and the sound quality may be degraded. For example, when the touch noise reducing technique is used for a wind noise, a voice that is a recoding target attenuates over a relatively long time period, whereby the sound quality is degraded. On the other hand, when the wind noise reducing technique is applied to a touch noise, the noise reducing effect is low. In Japanese Patent Application Publication Laid-open 2009-36831 A, a method is disclosed in which the absolute value of a difference component signal of low band frequency components of two microphones and the absolute value of a sum component signal thereof are compared with each other; and in a case where a state in which the absolute value of the difference component signal is larger than the sum of the absolute values of the sum component signals is continued for a predetermined period or more, a wind noise is regarded, and a wind noise reducing process is performed.

However, in a case where the operation of a wind noise reducing unit (an HPF in Japanese Patent Application Publication Laid-open 2009-36831 A) is started after the continuation of the state for a predetermined period or more is determined, the wind noise is not reduced during the predetermined period. In addition, in Japanese Patent Application Publication Laid-open 2009-36831 A, a reduction unit used for a touch noise is not disclosed. Therefore, according to the method disclosed in Japanese Patent Application Publication Laid-open 2009-36831 A, there is a problem in that the effect of reduction in both the wind noise and the touch noise is not sufficient.

The seventh and eighth embodiments may employ any one of the configurations described in the following 1) to 3).

1) A noise eliminating device including:

a first sound collecting unit configured to acquire a first audio signal;

a second sound collecting unit configured to acquire a second audio signal;

a first calculator configured to calculate a first difference signal that is a difference between a component of a first frequency band of the first audio signal and a component of the first frequency band of the second audio signal and a first sum signal that is a sum thereof;

a second calculator configured to calculate a second difference signal that is a difference between a component of a second frequency band of the first audio signal and a component of the second frequency band of the second audio signal and a second sum signal that is a sum thereof;

a first noise reduction processor configured to perform a first noise reducing process for the first audio signal and the second audio signal and outputs a first reduction processing signal;

a second noise reduction processor configured to perform a second noise reducing process for the first audio signal and the second audio signal and outputs a second reduction processing signal;

a switching unit configured to select and outputs either the first reduction processing signal or the second reduction processing signal;

a first controller configured to determine whether or not the first reduction processing signal is selected based on the amplitude of the first difference signal and the amplitude of the first sum signal, and performs control of the switching unit to output the first reduction processing signal in a case where the first reduction processing signal is determined to be selected; and a second controller configured to control the second noise reduction processing unit based on the amplitude of the second difference signal and the amplitude of the second sum signal.

2) A noise eliminating method including:

calculating a first difference signal that is a difference between a component of a first frequency band of a first audio signal of one channel out of a plurality of audio signals input from a plurality of channels and a component of the first frequency band of a second audio signal of another channel and a first sum signal that is a sum thereof;

calculating an amplitude of the first difference signal;

calculating an amplitude of the first sum signal;

calculating a second difference signal that is a difference between a component of a second frequency band of the first audio signal and a component of the second frequency band of the second audio signal and a second sum signal that is a sum thereof;

calculating an amplitude of the second difference signal;

calculating an amplitude of the second sum signal; calculating a first reduction processing signal by performing a first noise reducing process for the first audio signal and the second audio signal;

calculating a second reduction processing signal by performing a second noise reducing process for the first audio signal and the second audio signal;

selecting and outputting either the first reduction processing signal or the second reduction processing signal;

determining whether or not the first reduction processing signal is selected based on the amplitude of the first difference signal and the amplitude of the first sum signal and performing control to output the first reduction processing signal in a case where the first reduction processing signal is determined to be selected; and controlling the second noise reducing process based on the amplitude of the second difference signal and the amplitude of the second sum signal.

3) A noise eliminating program that allows a computer to perform a noise eliminating method for eliminating noises, the noise eliminating program including:

calculating a first difference signal that is a difference between a component of a first frequency band of a first audio signal of one channel out of a plurality of audio signals input from a plurality of channels and a component of the first frequency band of a second audio signal of another channel and a first sum signal that is a sum thereof;

calculating an amplitude of the first difference signal;

calculating an amplitude of the first sum signal;

calculating a second difference signal that is a difference between a component of a second frequency band of the first audio signal and a component of the second frequency band of the second audio signal and a second sum signal that is a sum thereof;

calculating an amplitude of the second difference signal;

calculating an amplitude of the second sum signal;

calculating a first reduction processing signal by performing a first noise reducing process for the first audio signal and the second audio signal;

calculating a second reduction processing signal by performing a second noise reducing process for the first audio signal and the second audio signal;

selecting and outputting either the first reduction processing signal or the second reduction processing signal;

determining whether or not the first reduction processing signal is selected based on the amplitude of the first difference signal and the amplitude of the first sum signal and performing control to output the first reduction processing signal in a case where the first reduction processing signal is determined to be selected; and controlling the second noise reducing process based on the amplitude of the second difference signal and the amplitude of the second sum signal.

According to this embodiment, a wind noise and a touch noise are accurately determined, and any one thereof can be reduced.

Seventh Embodiment

Figure 12:
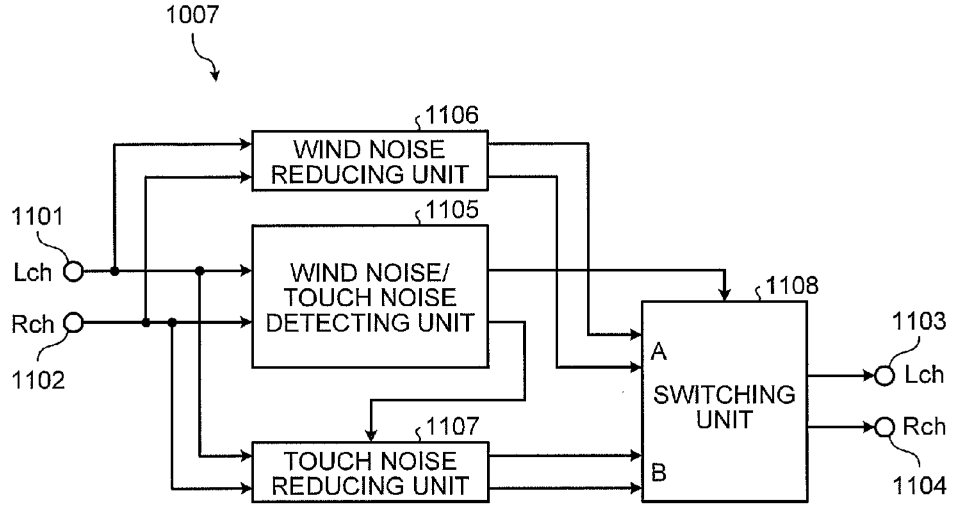
FIG. 12 is a configuration diagram of a noise eliminating device according to a seventh embodiment.

FIG. 12 is a diagram that illustrates the configuration of a noise eliminating device according to seventh embodiment. Audio signals of left and right channels Lch and Rch of stereo transmitted from two microphones, which are not illustrated in the figure and arranged in a casing of a portable-type voice recording device, are converted from analog to digital; and the converted signals are input from input terminals 1101 and 1102. The two microphones correspond to first and second sound collecting units, and the audio signals of the left and right channels correspond to first and second audio signals.

Figure 13:
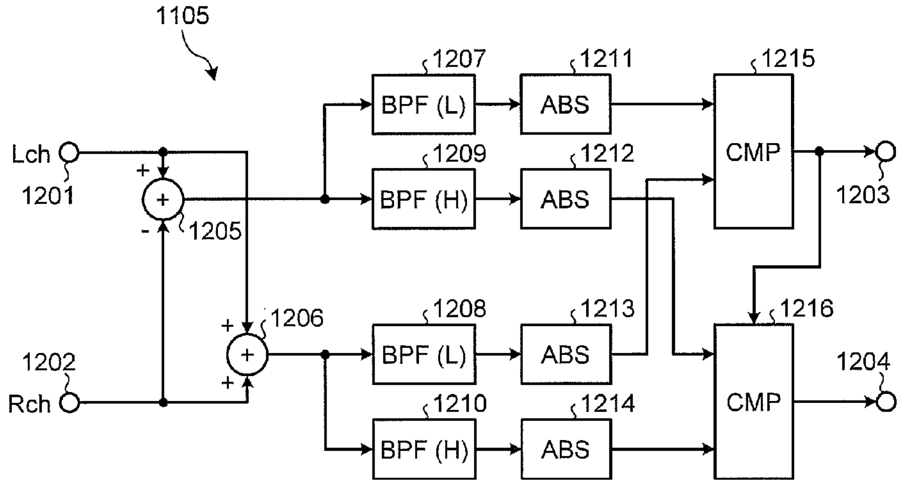
FIG. 13 is a configuration diagram of a wind noise/touch noise detecting unit according to the seventh embodiment.

The noise eliminating device 1007 is equipped with: a wind noise/touch noise detecting unit 1105; a wind noise reducing unit 1106; a touch noise reducing unit 1107; a switching unit 1108, input terminals 1101 and 1102, and output terminals 1103 and 1104. The noise eliminating device 1007 may be realized by an analog circuit, a digital circuit, and the like, software of a central processing unit (CPU), a digital signal processor (DSP), or the like, or a combination thereof. An audio signal of the left channel Lch received from the left microphone is input to the input terminal 1101. An audio signal of the right channel Rch received from the right microphone is input to the input terminal 1102. The audio signal of each channel is input to the wind noise/touch noise detecting unit 1105, the wind noise reducing unit 1106 that is a first noise reduction processing unit, and the touch noise reducing unit 1107 that is a second noise reduction processing unit. From the wind noise/touch noise detecting unit 1105, a signal used for controlling the touch noise reduction is output to the touch noise reducing unit 1107. In addition, a control signal used for switching between an output signal of the wind noise reducing unit 1106 and an output signal of the touch noise reducing unit 1107 is output to the switching unit 1108. Furthermore, the wind noise/touch noise detecting unit 1105 controls the turning-on/turning-off of the operation of the wind noise reducing unit 1106. The output signal of the wind noise reducing unit 1106 is one input (input A) of the switching unit 1108. The output signal of the touch noise reducing unit 1107 is the other input (input B) of the switching unit 1108. The inputs A and B are output by the switching unit 1108 in a switching manner. The output of the switching unit 1108 is input to an encoding unit not illustrated in the figure, and compression encoding or the like is performed for the input, and a resultant signal is recorded on a recording medium. Alternatively, the input signal is converted to an analog signal by a D/A conversion unit, and the converted analog signal is output to a speaker or the like. FIG. 13 is a diagram that illustrates the internal configuration of the wind noise/touch noise detecting unit 1105. The audio signals of the left and right channels Lch and Rch input from the input terminals 1101 and 1102 illustrated in FIG. 12 are input from the input terminals 1201 and 1202. Each signal is input to a subtracter 1205 and an adder 1206, and a difference signal and a sum signal are generated through subtraction and addition thereof. The difference signal that is the output of the subtracter 1205 is input to band pass filters 1207 and 1209. The sum signal that is the output of the adder 1206 is input to band pass filters 1208 and 1210. Here, the passband of the band pass filter 1207 is relatively low, and the passband of the band pass filter 1209 is higher than that of the band pass filter 1207. For example, the passband of the band pass filter 1207 is 50 Hz to 300 Hz, and the passband of the band pass filter 1209 is 500 Hz to 1.5 KHz. The band pass filter 1208 and the band pass filter 1207 have the same characteristics, and the band pass filter 1210 and the band pass filter 1209 have the same characteristics.

A first difference signal is calculated using a combination of the subtracter 1205 and the band pass filter 1207. A first sum signal is calculated using a combination of the adder 1206 and the band pass filter 1208. A first calculation unit is configured by the subtracter 1205, the band pass filter 1207, the adder 1206, and the band pass filter 1208. A second difference signal is calculated using a combination of the subtracter 1205 and the band pass filter 1209. A second sum signal is calculated using a combination of the adder 1206 and the band pass filter 1210. A second calculation unit is configured by the subtracter 1205, the band pass filter 1209, the adder 1206, and the band pass filter 1210. The pass band of the band pass filter 1207 that is set to 50 Hz to 300 Hz is a band lower than a band used in a conventional example of a case similar thereto. In the conventional example, the pass band is set to a band of 1 KHz or less. Regarding the wind noise, even in a case where the passband is set to 50 Hz to 300 Hz, there are many low band frequency components in that band, and accordingly, a signal having relatively large amplitude is output as the output of the filter. On the other hand, while the touch noise is an impulse-pattern noise and has a wide frequency band, the touch noise has a small low-band frequency component of 50 Hz to 300 Hz, and the output amplitude of the band pass filter having the passband of 50 Hz to 300 Hz is almost zero.

The audio signals input to the two microphones that are arranged to be close to each other are signals having low band frequency components of several KHz or less to be approximately the same and are signals having a difference in accordance with a distance between the microphones for a higher frequency. When the speed of sound in the air is 340 m/second, the wavelength of the signal having a frequency of 1 KHz is 34 cm. Thus, in a case where the distance between the two microphones is 2 cm, signal waveforms that are approximately the same are input. Therefore, the difference signal is almost zero. On the other hand, in a case where the wavelength of the signal having a frequency of 10 KHz is 3.4 cm, and the signal having this frequency arrives in the horizontal direction parallel to the two microphones, signal waveforms having opposite phases are input to the two microphones. Therefore, the difference signal thereof is a signal having large amplitude.

A signal that is generated in a microphone due to a wind noise is generated in accordance with a turbulent flow due to a wind, and the states of the turbulent flows in microphones are different from each other even in a case where the microphones are located to be close to each other; and a difference signal thereof has large amplitude even in the low frequency band. As the frequency band of a wind noise signal, a component of 1 KHz or less is the main, and the frequency band also includes frequency components of several tens Hz or less. A touch noise is generated by a person's finger or the like being brought into contact with the casing, is an impulse-pattern noise, has a wide frequency band, and has small low frequency components of 500 Hz or less. The touch noises are signals having different waveforms even in a case where two microphones are located to be close to each other. The touch noise is considered to propagate through the casing and arrive at the microphone, and the difference is considered to occur when the vibration thereof is delivered to the microphones. The output signal of the band pass filter 1207 to which the difference signal is input is almost zero for the audio signals but is an output signal having relatively large amplitude for the wind noises. In addition, the output signal is almost zero for the touch signal. Similarly, the output signal of the band pass filter 1209 to which the difference signal is input is almost zero for the audio signals but is an output signal having relatively large amplitude for the wind noise. Furthermore, also for the touch noise, an output signal having relatively large amplitude is formed. The output signal of the band pass filter 1208 to which the sum signal is input is a signal according to the frequency distribution of the input signal for the audio signals and is an output signal having relatively large amplitude for the wind noise. In addition, the output signal is almost zero for the touch signal. Similarly, the output signal of the band pass filter 1210 to which the sum signal is input is a signal according to the frequency distribution of the input signal for the audio signals and is an output signal having relatively large amplitude for the wind noise. Furthermore, also for the touch noise, an output signal having relatively large amplitude is formed. The outputs of the band pass filters 1207, 1209, 1208, and 1210 are input to absolute value implementing units 1211, 1212, 1213, and 1214, and the absolute values thereof are calculated and are output. The use of the absolute values is for easy comparison of amplitudes in the comparators 1215 and 1216. Instead of the absolute value, a value acquired by calculating the square thereof using the square calculator may be output. Furthermore, data acquired by smoothing signals of which values are set to the absolute values thereof along the time axis by using a low pass filter not illustrated in the figure or the like may be configured to be output. The output signal of the absolute value implementing unit 1211 and the output signal of the absolute value implementing unit 1213 are input to the comparator 1215. Similarly, the output signal of the absolute value implementing unit 1212 and the output signal of the absolute value implementing unit 1214 are input to the comparator 1216. In the comparator 1215, the output signal (an absolute-value signal relating to the first difference signal) Sdiff_L of the absolute value implementing unit 1211 and the output signal (an absolute value signal relating to the first sum signal) Ssum_L of the absolute value implementing unit 1213 are compared with each other. In addition, the magnitude of the output signal Sdiff_L is referred to. In a case where the following Equations (1) and (2) are satisfied for predetermined coefficients k_L (k_L, for example is 0.5) and a predetermined threshold Vth_L, the comparator 1215 outputs an output signal CMP_L=1; and outputs an output signal CMP_L=0 in the other cases.

$$Sdiff\_L \geq k\_L \times Ssum\_L \tag{1}$$

$$Sdiff\_L \geq Vth\_L \tag{2}$$

The output signal CMP_L is output from the output terminal 1203.

In the comparator 1216, the output signal (an absolute-value signal relating to the second difference signal) Sdiff_H of the absolute value implementing unit 1212 and the output signal (an absolute value signal relating to the second sum signal) Ssum_H of the absolute value implementing unit 1214 are compared with each other. In addition, the magnitude of the output signal Sdiff_H is referred to. Furthermore, the output signal CMP_L of the comparator 1215 is referred to. In a case where the following Equations (3), (4), and (5) are satisfied for predetermined coefficients k_H (k_H, for example is 0.5) and a predetermined threshold Vth_H, the comparator 1216 outputs an output signal CMP_H=1 and outputs an output signal CMP_H=0 in the other cases.

$$Sdiff\_H \geq k\_H \times Ssum\_H \tag{3}$$

$$Sdiff\_H \geq Vth\_H \tag{4}$$

$$CMP\_L = 0 \tag{5}$$

The output signal CMP_H is output from the output terminal 1204.

The comparator 1215 generates the output signal CMP_L based on the amplitude of a first difference signal that is a difference between the first audio signal and the second audio signal of the first frequency band and the amplitude of a first sum signal that is a sum thereof. In a case where the amplitude of the first difference signal is a predetermined threshold or more and is amplitude that is a predetermined rate of the amplitude of the first sum signal or more, the output signal CMP_L=1 is output. As described above, in this embodiment, the predetermined first frequency band is set to the passband 50 Hz to 300 Hz of the band pass filters 1207 and 1208. The conditions for the amplitude of the sum signal and the amplitude of the difference signal in this frequency band are satisfied only for the case of a wind noise.

The comparator 1216 generates the output signal CMP_H based on the amplitude of a second difference signal that is a difference between the first audio signal and the second audio signal of the second frequency band and the amplitude of a second sum signal that is a sum thereof. In a case where the amplitude of the second difference signal is a predetermined threshold or more, the amplitude of the second difference signal is amplitude that is a predetermined rate of the amplitude of the second sum signal or more, and the output signal output from the comparator 1215 is CMP_L=0, the output signal CMP_H=1 is output. As described above, in this embodiment, the predetermined second frequency band is set to the passband 500 Hz to 1.5 KHz of the band pass filters 1209 and 1210. The conditions for the amplitude of the sum signal and the amplitude of the difference signal in this frequency band are satisfied for the case of a wind noise and the case of a touch noise. By further applying the condition of CMP_L=0, the conditions are satisfied only for the case of a touch noise.

A first control unit is configured by the absolute value implementing units 1211 and 1213 and the comparator 1215. A second control unit is configured by the absolute value implementing units 1212 and 1214 and the comparator 1216.

Although the wind noise/touch noise detecting unit 1105 illustrated in FIG. 13 is configured to calculate a difference signal and a sum signal of the input signals and to input the difference signal and the sum signal, which have been calculated, to the band pass filters; it may be configured such that input signals are first input to the band pass filters, and a difference signal and a sum signal of the outputs of the band pass filters are acquired. In such a case, the audio signal of the left channel Lch received from the input terminal 1201 is input to the band pass filters 1207 and 1209, and the audio signal of the right channel Rch received from the input terminal 1202 is input to the band pass filters 1208 and 1210. A difference signal and a sum signal of the outputs of the band pass filters 1207 and 1208 are calculated, and the difference signal is input to the absolute value implementing unit 1211. The sum signal is input to the absolute value implementing unit 1213. In addition, a difference signal and a sum signal of the outputs of the band pass filters 1209 and 1210 are calculated, and the difference signal is input to the absolute value implementing unit 1212. The sum signal is input to the absolute value implementing unit 1214. The other configurations are the same as those illustrated in FIG. 13.

Figure 14:
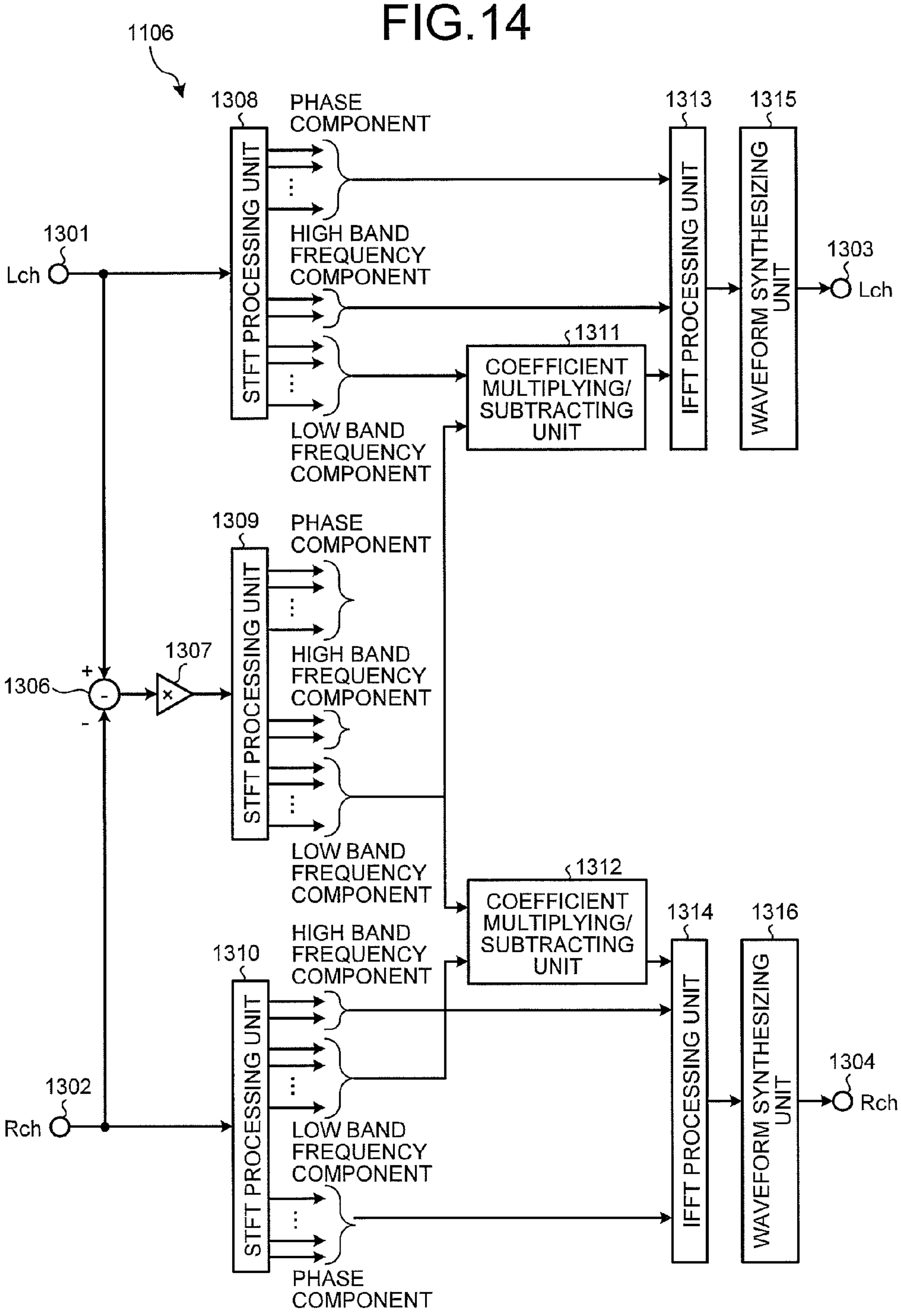
FIG. 14 is a configuration diagram of a wind noise reducing unit according to the seventh embodiment.

FIG. 14 is a diagram that illustrates an example of the internal configuration of the wind noise reducing unit 1106. Incidentally, the internal configuration of the wind noise reducing unit 1106 is not limited to the configuration illustrated in FIG. 14. For example, a wind noise reducing unit having the same configuration as that of the noise eliminating device according to any one of first to sixth embodiments described above may be used. The audio signals of the left and right channels Lch and Rch received from the input terminals 1101 and 1102 illustrated in FIG. 12 are input from the input terminals 1301 and 1302. The wind noise reducing unit 1106 reduces the wind noise by eliminating a low band frequency component of the difference signal of the audio signals of the left and right channels Lch and Rch from the frequency domain as a wind noise component.

The audio signals of the left and right channels Lch and Rch are respectively input to STFT processing units 1308 and 1310. In addition, a difference signal of the audio signals of the left and right channels Lch and Rch is calculated by the subtracter 1306 and is multiplied by ½ by a constant multiplier 1307 and is input to an SIFT processing unit 1309.

The SIFT (short time Fourier transform) processing unit forms input signals as a frame altogether in a frame having a predetermined length while shifting the input signal for every predetermined time; performs the process of applying a predetermined time window to each frame; performs an FFT (fast Fourier transform) process for the signals to which the time window is applied; and outputs a phase value and an amplitude value at each frequency of each frame.

In the case of an FFT of the 256th degree, 128 amplitude values |Y(t, k×f0)|(K=0 to 127) and phase values ϕy(k×f0) (K=0 to 127) are output. For the signal of the left channel Lch, |YL(t, k×f0)|, ϕyL(k×f0) is represented, for the signal of the right channel Rch, |YR(t, k×f0)|, ϕyR(k×f0) is represented, and for the difference signal, |Ys(t, k×f0)|, ϕys(k×f0) is represented. The data of amplitude values of the low frequency band of the signal of the left channel Lch and the difference signal is input to a coefficient multiplying/subtracting unit 1311. For example, as 32 data values of the low band, there are |YL(t, k×f0)|, |Ys(t, k×f0)|(K=0 to 31). The coefficient multiplying/subtracting unit 1311 multiplies each data value |Ys(t, k×f0)|(K=0 to 31) by a predetermined coefficient C. Here, C is a value around one.

Next, a result of the multiplication is subtracted from the amplitude value data of the signal of the left channel Lch. Here, in a case where the result of the multiplication is negative as represented in the following Equation (6), the result is substituted with zero.

$$|YL(t,k\times f0)|-C\times|Ys(t,k\times f0)|<0 \quad (6)$$

This result of the subtraction, the amplitude value data |YL(t, k×f0)| of the high frequency band of the signal of the left channel Lch (K=32 to 127) and the phase value ϕyL(k×f0) (K=0 to 127) of the signal of the left channel Lch are input to an IFFT processing unit 1313. The IFFT processing unit 1313 performs an IFFT (inverse FFT) process by using the amplitude information and the phase information.

The output of the IFFT processing unit 1313 is input to a waveform synthesizing unit 1315. The waveform synthesizing unit 1315 performs an inverse windowing process and a waveform synthesizing process and outputs the audio signal of the left channel Lch from an output terminal 1303. Similarly, the amplitude value data of the low frequency band of each one of the signal of the right channel Rch and the difference signal is input to a coefficient multiplying/subtracting unit 1312; and coefficient multiplication and subtraction is performed for the amplitude value data; and resultant data is output. This result of the subtraction and the phase value ϕyR(k×f0) (K=0 to 127) of the signal of the right channel Rch are input to an IFFT processing unit 1314. The IFFT processing unit 1314 performs an IFFT (inverse FFT) process by using the amplitude information and the phase information. The output of the IFFT processing unit 1314 is input to a waveform synthesizing unit 1316, and the same process as that of the waveform synthesizing unit 1315 is performed, and the audio signal of the right channel Rch is output from an output terminal 1304.

The wind noise reducing unit 1106 is controlled so as to operate only during a period in which the output signal CMP_L of the comparator 1215 is one and to stop the operation during a period in which the output signal CMP_L is zero. The wind noise reducing unit 1106 has a relatively large amount of calculation and has high power consumption at the time of the operation. Since the wind noise is not generated all the time, by stopping the operation during a period in which the wind noise is not generated, the power consumption can be reduced.

Figure 15:
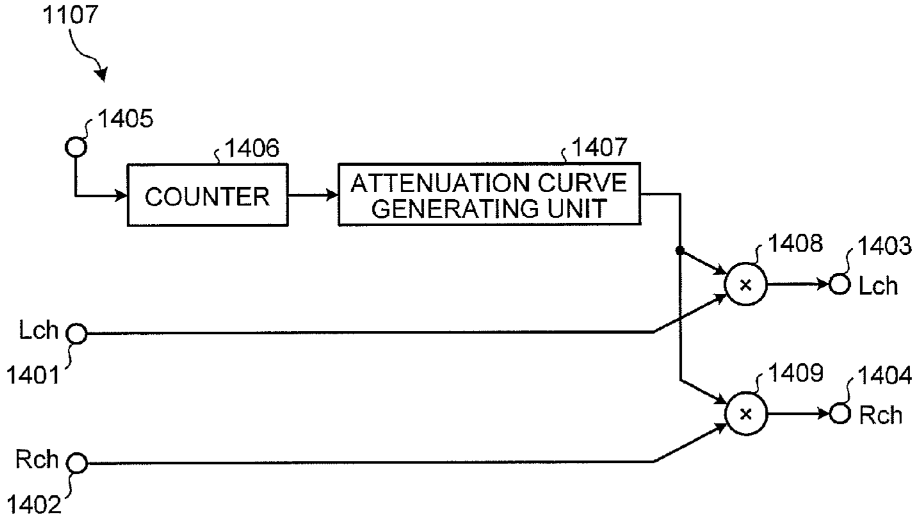
FIG. 15 is a configuration diagram of a touch noise reducing unit according to the seventh embodiment.

FIG. 15 is a diagram that illustrates the internal configuration of a touch noise reducing unit 1107. Audio signals of the left and right channels Lch and Rch received from the input terminals 1101 and 1102 illustrated in FIG. 12 are input to input terminals 1401 and 1402. In addition, the output signal CMP_H that is a result of the detection of a touch noise is input to an input terminal 1405 from the wind noise/touch noise detecting unit 1105 illustrated in FIG. 12. The touch noise reducing unit 1107 attenuates audio signals only for a predetermined period from the time at which a touch noise is detected.

Figure 16:
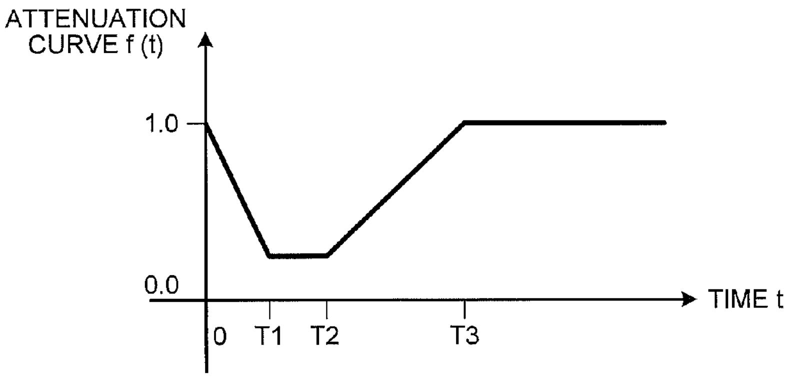
FIG. 16 is a graph that illustrates the attenuation characteristics of the touch noise reducing unit according to the seventh embodiment.

The rise of the input signal input to the input terminal 1405 is detected, and then, a counter 1406 is reset. Thereafter, counting up is performed in synchronization with the sampling cycle of audio signals. Then, when the counted value arrives at a value corresponding to a predetermined time T3, the counting up is stopped, and the counted value is maintained. The counted value of the counter 1406 is input to an attenuation curve generating unit 1407. The attenuation curve generating unit 1407 generates an attenuation coefficient corresponding to an attenuation curve illustrated in FIG. 16 in accordance with the input counted value. In other words, the attenuation coefficient: is decreased in accordance with a counted value up to a counted value corresponding to a predetermined time T1; is maintained until time T2; and is increased until time T3. More specifically, a ROM (read only memory) or the like can be configured in which data relating to the input counted value is set as the address, and a value corresponding to the attenuation coefficient is output.

The attenuation coefficient output from the attenuation curve generating unit 1407 is input to the multipliers 1408 and 1409. The audio signal input from the input terminal 1401: is input to the other input of the multiplier 1408; is multiplied by the attenuation coefficient; and is output from the output terminal 1403. Similarly, the audio signal input from the input terminal 1402 is input to the other input of the multiplier 1409, is multiplied by the attenuation coefficient, and is output from the output terminal 1404.

Figure 17:
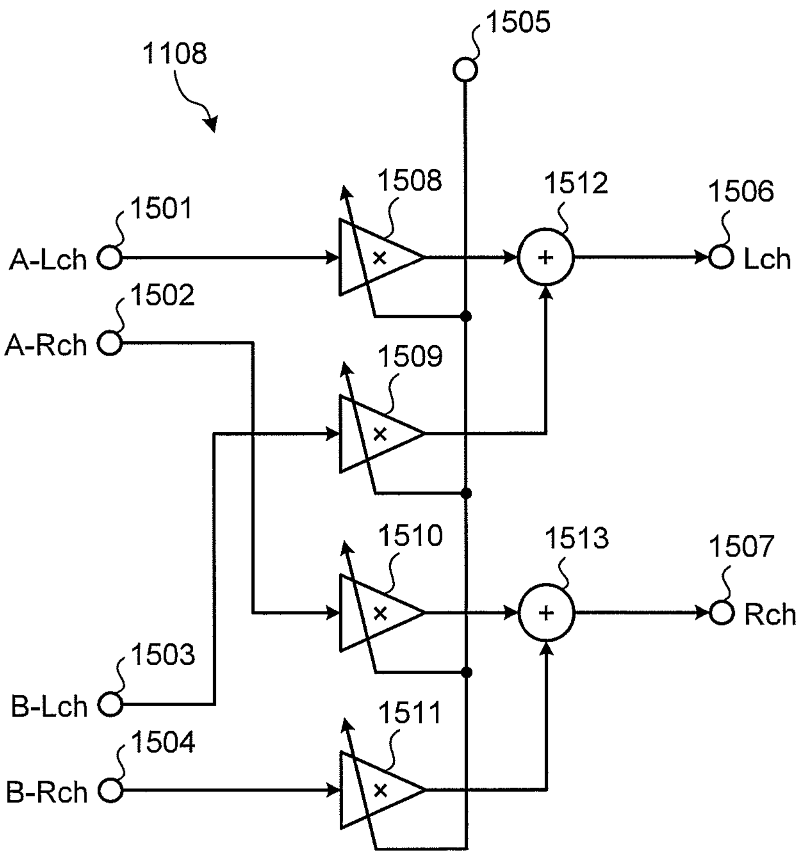
FIG. 17 is a configuration diagram that illustrates a switching unit according to the seventh embodiment.

FIG. 17 is a diagram that illustrates the internal configuration of the switching unit 1108. Audio signals of the left and right channels Lch and Rch that are the output signals of the wind noise reducing unit 1106 illustrated in FIG. 12 are input from input terminals 1501 and 1502. In addition, audio signals of the left and right channels Lch and Rch that are the output signals of the touch noise reducing unit 1107 illustrated in FIG. 12 are input from input terminals 1503 and 1504. Furthermore, a wind noise detection signal CMP_L, received from the wind noise/touch noise detecting unit 1105 illustrated in FIG. 12, is input from an input terminal 1505. The switching unit 1108 switches the input signal input from the wind noise reducing unit 1106 and the input signal input from the touch noise reducing unit 1107, and outputs the signals.

The audio signal received from the input terminal 1501 is input to a coefficient multiplier 1508. The audio signal received from the input terminal 1502 is input to a coefficient multiplier 1510. As control signals for the coefficient multipliers 1508 and 1510, the wind noise detection signal CMP_L received from the input terminal 1505 is input. The coefficient multipliers 1508 and 1510 perform multiplication using a multiplication coefficient of "1" when the wind noise detection signal CMP_L=1 and perform multiplication using a multiplication coefficient of "0" when the wind noise detection signal CMP_L=0.

The audio signal received from the input terminal 1503 is input to the coefficient multiplier 1509. The audio signal received from the input terminal 1504 is input to the coefficient multiplier 1511. The coefficient multipliers 1509 and 1511 perform multiplication using a multiplication coefficient of "0" when the wind noise detection signal CMP_L=1 and perform multiplication using a multiplication coefficient of "1" when the wind noise detection signal CMP_L=0. The output of the coefficient multiplier 1508 and the output of the coefficient multiplier 1509 are input to an adder 1512 and are operated to be added together; and a result of the addition is output from an output terminal 1506. The output of the coefficient multiplier 1510 and the output of the coefficient multiplier 1511 are input to an adder 1513 and are operated to be added together; and a result of addition is output from an output terminal 1507.

Accordingly, the output signal of the wind noise reducing unit is selected to be output during a period in which a wind noise is detected, and CMP_L=1; and the output signal of the touch noise reducing unit is selected to be output during a period in which a wind noise is not detected, and CMP_L=0.

In addition, the signal CMP_L received from the input terminal 1505 may be input to a time constant unit not illustrated in the figure; and the output signal $\alpha$ may be input to the coefficient multipliers 1508, 1509, 1510, and 1511. In a case where the signal CMP_L rises from "0" to "1", the time constant unit increases the output signal to be $\alpha=0$, $\alpha=0.2$, $\alpha=0.4$, $\alpha=0.6$, $\alpha=0.8$, and $\alpha=1.0$ in a stepwise manner in synchronization with the sampling cycle of the audio signal. On the other hand, in a case where the signal CMP_L falls from "1" to "0", the time constant unit decreases the output signal to be $\alpha=1.0$, $\alpha=0.8$, $\alpha=0.6$, $\alpha=0.4$, $\alpha=0.2$, and $\alpha=0$ in a stepwise manner in synchronization with the sampling cycle of the audio signal. The output signal $\alpha$ is used in the coefficient multipliers 1508 and 1510 as a multiplication coefficient and is used in the coefficient multipliers 1509 and 1511 as $(1-\alpha)$ as a multiplication coefficient. As above, by changing the output signal in a stepwise manner, the sense of strangeness accompanied with the switching can be decreased.

As above, in this embodiment, by using the signal CMP_L that is generated based on the amplitude of the first difference signal that is a difference between first-frequency band components of the first and second audio signals and the amplitude of a first sum signal that is a sum thereof, a signal processed by a wind noise reducing process that is the first noise reducing process is selected and is output. In addition, the touch noise reducing process that is the second noise reducing process is controlled based on: the amplitude of the second difference signal that is a difference between second-frequency band components of the first and second audio signals; the amplitude of a second sum signal that is a sum thereof; and the signal CMP_L.

In addition, during a period in which the signal CMP_L is "0", the operation of the wind noise reducing unit 1106 is stopped.

According to this embodiment, the wind noise reducing process is not erroneously performed for a touch noise, and the touch noise reducing process is not erroneously performed for a wind noise. As a result, a reduction process matching the characteristics of the noise can be performed, and accordingly, the degradation of the sound quality can be suppressed to be minimal. In addition, since the operation of the wind noise reducing unit 1106 can be stopped when the wind noise is not generated, and thus the power consumption can be reduced.

In addition, the signal CMP_H may be generated by the comparator 1216 arranged inside the wind noise/touch noise detecting unit 1105 illustrated in FIG. 13 without requiring the condition of Equation (5). In such a case, the touch noise reducing process can be performed even in the case of the wind noise, which is a disadvantage from the viewpoint of the power consumption. However, since the output signal output from the wind noise reducing unit 1106 is selected by the switching unit 1108, there is no influence on the output signal.

Eighth Embodiment

Next, a noise eliminating device according to eighth embodiment of the present invention will be described with reference to the drawings.

Figure 18:
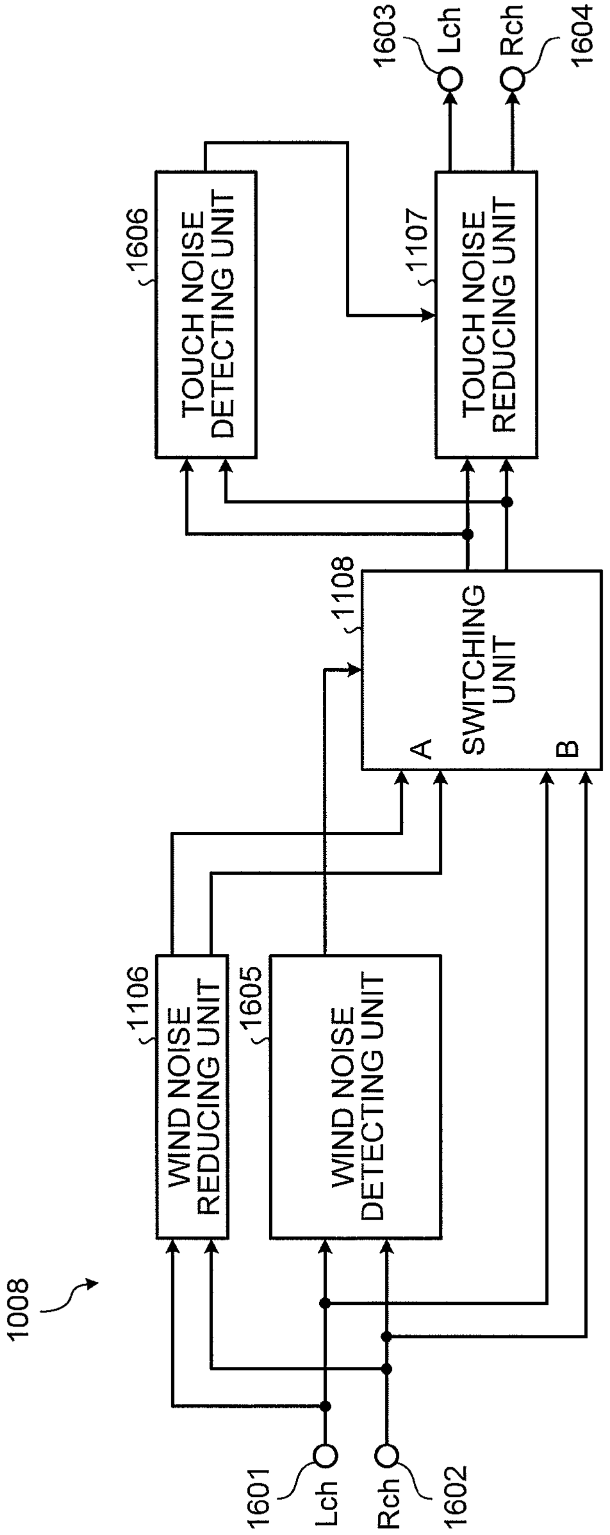
FIG. 18 is a configuration diagram of a noise eliminating device according to an eighth embodiment.

FIG. 18 is a diagram that illustrates the configuration of the noise eliminating device 1008 according to eighth embodiment, and the same or corresponding reference numeral is assigned to the same or corresponding part as that, which is illustrated in FIG. 12, according to seventh embodiment. Similar to seventh embodiment, audio signals of left and right channels Lch and Rch of stereo transmitted from two microphones are converted from analog to digital, and the converted signals are input from input terminals 1601 and 1602. The input audio signals of the left and right channels Lch and Rch are input to an input B of a switching unit 1108 by a wind noise reducing unit 1106 that is a first noise reduction processing unit and a wind noise detecting unit 1605. The wind noise reducing unit 1106 is the same as the wind noise reducing unit 1106, which is illustrated in FIG. 12, according to seventh embodiment. In addition, in a case where the input to the wind noise reducing unit 1106 is output with a delay due to the wind noise reducing process, a delay unit not illustrated in the figure may be arranged before the input B of the switching unit 1108 so as to compensate for the delay.

The output signal of the wind noise reducing unit 1106 is an input A of the switching unit 1108. The switching unit 1108 is the same as the switching unit 1108, which is illustrated in FIG. 12, according to seventh embodiment. The wind noise detecting unit 1605 detects whether or not there is a wind noise and outputs the output signal of the wind noise reducing unit 1106 and a control signal used for switching between signals transmitted from the input terminals 1601 and 1602 to the switching unit 1108

The output signal of the switching unit 1108 is input to a touch noise detecting unit 1606 and a touch noise reducing unit 1107 that is a second noise reduction processing unit. The touch noise reducing unit 1107 is the same as the touch noise reducing unit 1107 illustrated in FIG. 12, and the output signals thereof are output from output terminals 1603 and 1604. The touch noise detecting unit 1606 detects a touch noise and outputs a signal used for controlling the reduction of the touch noise to the touch noise reducing unit 1107.

Figure 19:
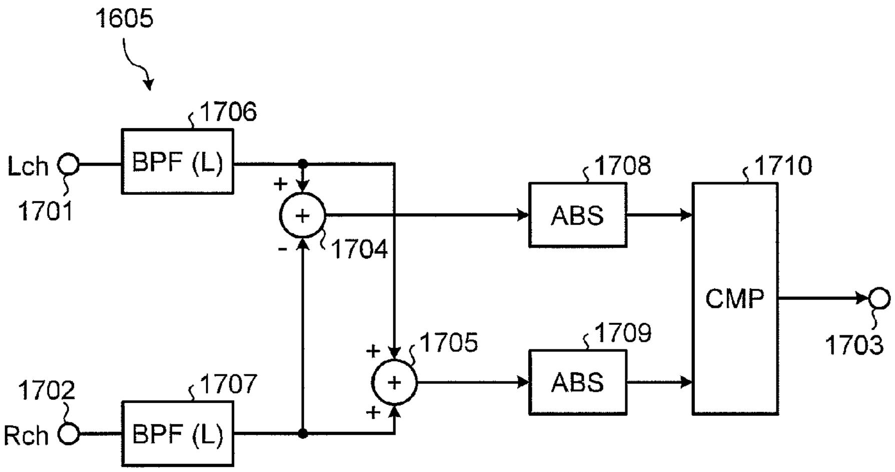
FIG. 19 is a configuration diagram of a wind noise detecting unit according to the eighth embodiment.

FIG. 19 is a diagram that illustrates the internal configuration of the wind noise detecting unit 1605. The audio signals of the left and right channels Lch and Rch that are input from the input terminals 1601 and 1602 illustrated in FIG. 18 are input from input terminals 1701 and 1702. Each signal is input to band pass filters 1706 and 1707. The band pass filters 1706 and 1707 are the same as the band pass filter 1207 illustrated in FIG. 13, and the passband thereof is 50 Hz to 300 Hz. The outputs of the band pass filters 1706 and 1707 are input to a subtracter 1704 and an adder 1705, and a difference signal and a sum signal are generated by performing subtraction and addition thereof. The values of the difference signal and the sum signal are set to the absolute values thereof respectively by absolute value implementing units 1708 and 1709 and are input to a comparator 1710. A first calculation unit is configured by the band pass filters 1706 and 1707, the subtracter 1704, and the adder 1705.

In the comparator 1710, the output signal (an absolute-value signal relating to a first difference signal) Sdiff_L of the absolute value implementing unit 1708 and the output signal (an absolute value signal relating to a first sum signal) Ssum_L of the absolute value implementing unit 1709 are compared with each other. In addition, the magnitude of the absolute value signal input Sdiff_L relating to the first difference signal is referred to. In a case where the following Equations (7) and (8) are satisfied for predetermined coefficients k_L (for example, k_L is 0.5) and a predetermined threshold Vth_L, the comparator 1710 outputs an output signal CMP_L=1 from the output terminal 1703 and outputs an output signal CMP_L=0 in other cases.

$$Sdiff\_L \geq k\_L \times Ssum\_L \quad (7)$$

$$Sdiff\_L \geq Vth\_L \quad (8)$$

A first control unit is configured by the absolute value implementing units 1708 and 1709 and the comparator 1710.

The output signal CMP_L of the comparator 1710 is input to the input terminal 1504 of the switching unit 1108. The internal configuration of the switching unit 1108 is illustrated in FIG. 17 and performs the operation as described in seventh embodiment.

As described above, in the difference signals of the low frequency band, particularly, a frequency band of 300 Hz or less of the audio signals received by two microphones that are located close to each other, the audio signal and the touch noise component are almost zero, and the wind noise is the major component. Accordingly, the output signal CMP_L output from the wind noise reducing unit 1106 is CMP_L=1 only in a case where there is a wind noise, and the output signal CMP_L=0 is maintained in a case where there is no wind noise but there is an audio signal or a touch noise.

The switching unit 1108 selects and outputs the input A in a case where CMP_L=1, and selects and outputs the input B in a case where CMP_L=0. In addition, similar to seventh embodiment, in the case where CMP_L=0, the operation of the wind noise reducing unit 1106 is stopped.

Figure 20:
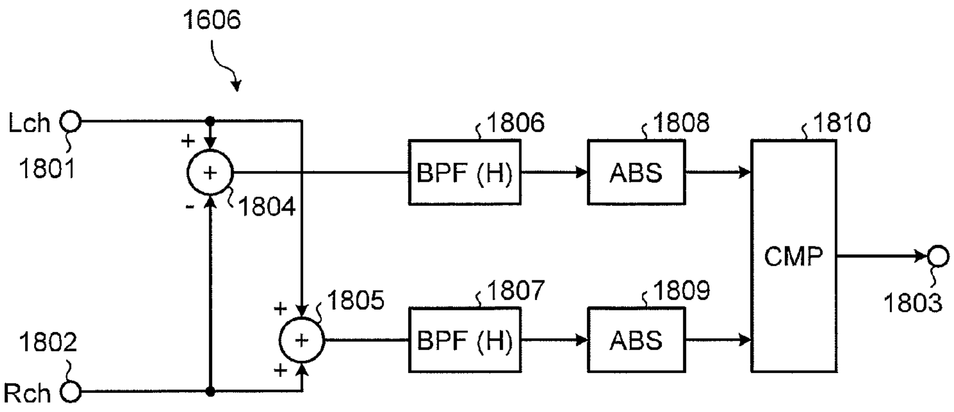
FIG. 20 is a configuration diagram of a touch noise detecting unit according to the eighth embodiment.

FIG. 20 is a diagram that illustrates the internal configuration of the touch noise detecting unit 1606. Audio signals of the left and right channels Lch and Rch transmitted from the switching unit 1108 illustrated in FIG. 18 are input from input terminals 1801 and 1802. Each signal is input to a subtracter 1804 and an adder 1805, and a difference signal and a sum signal are generated through subtraction and addition thereof. The difference signal is input to a band pass filter 1806. The sum signal is input to a band pass filter 1807. The band pass filters 1806 and 1807 are the same as the band pass filter 1209 illustrated in FIG. 13, and the passband thereof is 500 Hz to 1.5 KHz. A second calculation unit is configured by the subtracter 1804, the adder 1805, and the band pass filters 1806 and 1807.

The values of the outputs of the band pass filters 1806 and 1807 are respectively set to the absolute values thereof by the absolute value implementing units 1808 and 1809 and are input to a comparator 1810.

In the comparator 1810, the output signal (an absolute-value signal relating to the second difference signal) Sdiff_H of the absolute value implementing unit 1808 and the output signal (an absolute value signal relating to the second sum signal) Ssum_H of the absolute value implementing unit 1809 are compared with each other. In addition, the magnitude of the absolute value signal Sdiff_H relating to the second difference signal is referred to.

In a case where the following Equations (9) and (10) are satisfied for predetermined coefficients k_H (k_H, for example is 0.5) and a predetermined threshold Vth_H, the comparator 1810 outputs an output signal CMP_H=1 from the output terminal 1803 and outputs an output signal CMP_L=0 in the other cases.

$$Sdiff\_H \geq k\_H \times Ssum\_H \quad (9)$$

$$Sdiff\_H \geq Vth\_H \quad (10)$$

A second control unit is configured by the absolute value implementing units 1808 and 1809 and the comparator 1810.

The output signal CMP_H is input to the touch noise reducing unit 1107. The touch noise reducing unit 1107 is the same as the touch noise reducing unit 1107 illustrated in FIG. 12 according to seventh embodiment, and the internal configuration thereof is illustrated in FIG. 15.

The output signal CMP_H is input to the input terminal 1405. The operation of the touch noise reducing unit 1107 is as described above.

The passband of the band pass filters 1806 and 1807 is 500 Hz to 1.5 KHz, and as described above, in a case where a difference signal between signals received by two microphones that are located to be close to each other is input, the amplitude of the output signal is almost zero for the audio signal. On the other hand, in a case where a difference signal is input for the touch noise, output signals having relatively high amplitude are formed. While output signals having relatively high amplitude are originally formed also for a wind noise, in this embodiment, the difference signal is a difference signal between signals in which the wind noise is reduced by the wind noise reducing unit 1106 arranged in the previous stage; and accordingly, the amplitude of the output signals due to the wind noise is small.

Accordingly, by comparing the absolute value relating to the second difference signal and the absolute value of the second sum signal with each other as described above by using the touch noise detecting unit 1606, only a touch noise can be detected. Furthermore, by operating the touch noise reducing unit based on the detected signal only when the touch noise is input, and accordingly the touch noise can be effectively reduced.

While the wind noise detecting unit 1605 illustrated in FIG. 19 is configured to calculate a difference signal and a sum signal after the band pass filter is applied thereto, a configuration may be employed in which a difference signal and a sum signal are first calculated as illustrated in FIGS. 13 and 20, and a band pass filter is then applied thereto. In addition, while the touch noise detecting unit 1606 illustrated in FIG. 20 is configured to calculate a difference signal and a sum signal first, and a band pass filter is applied thereto, a configuration may be employed in which a difference signal and a sum signal are calculated after the band pass filter is applied first as illustrated in FIG. 19.

The modifications described in seventh embodiment such as the substitution of the absolute value implementing unit with a square calculator or performing smoothing along the time axis using a low pass filter or the like for the signal of which the value is set to the absolute value thereof can be similarly made.

As above, in this embodiment, based on the amplitude of the first difference signal that is a difference between components of the predetermined first frequency band of the first and second audio signals and the amplitude of a first sum signal that is the sum thereof, a signal for which the wind noise reducing process that is the first noise reducing process has been performed and an audio signal for which the process has not been performed are selected and output. In addition, the second noise reducing process is performed for the output signals based on the amplitude of a second difference signal that is a difference between components of the predetermined second frequency band of a signal relating to the first audio signal and a signal relating to the second audio signal and the amplitude of a second sum signal that is the sum thereof. According to the embodiment, the wind noise reducing process is not erroneously performed for a touch noise, and the touch noise reducing process is not erroneously performed for a wind noise. As a result, a reduction process matching the characteristics of the noise can be performed, and accordingly, the degradation of the sound quality can be suppressed to be minimal. In addition, since the operation of the wind noise reducing unit can be stopped when the wind noise is not generated, whereby the power consumption can be reduced.

The above-described process for eliminating noises may be performed by a computer program. The above-described noise eliminating program may be supplied to a computer with being stored on various types of non-transitory computer readable medium. The non-transitory computer readable medium includes various types of tangible storage medium. Examples of the non-transitory computer readable medium include a magnetic recording medium (for example, a flexible disk, a magnetic tape, or a hard disk drive), a magneto-optical recording medium (for example, a magneto-optical disk), a CD-ROM (read only memory), a CD-R, a CD-R/W, and a semiconductor memory (for example, a mask ROM, a PROM (programmable ROM), an EEPROM (erasable PROM), a flash ROM, or a RAM (random access memory)).

In addition, the noise eliminating program may be supplied to the computer using various types of transitory computer readable medium. Examples of the transitory computer readable medium include an electric signal, an optical signal, and an electromagnetic wave. The transitory computer readable medium may supply the noise eliminating program to the computer through a wired communication path such as a wire or an optical fiber or a wireless communication channel.

Furthermore, not only a case where the function of the above-described embodiment is realized by the computer executing the noise eliminating program realizing the function of the above-described embodiment but also a case where the noise eliminating program realizes the function of the above-described embodiment in cooperation with an OS (operating system) or an application software operating on the computer is included in an embodiment of the present invention.

According to the present invention, a noise eliminating device, a noise eliminating method, and a noise eliminating program capable of effectively reducing a wind noise and minimizing the degradation of an audio signal is to be provided.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A noise eliminating device comprising:

a signal calculator configured to calculate a difference signal between a signal of one channel out of a plurality of signals input from a plurality of channels and a signal of another channel;

a variable filter unit configured to process the signals of the plurality of channels and output processed signals;

an adaptive filter unit configured to operate by receiving a composite signal of the difference signal and another signal as an input signal; and a unit configured to calculate an error signal between an output signal of the adaptive filter unit and a signal having correlation with the another signal being set as a desired signal, wherein characteristics of the adaptive filter are changed by using the error signal, and characteristics of the variable filter are changed in accordance with a change in the characteristics of the adaptive filter.

2. A noise eliminating device comprising:

a signal calculator that calculates a difference signal and a sum signal between a signal of one channel out of a plurality of signals input from a plurality of channels and a signal of another channel;

a variable filter unit configured to process the sum signal and output a processed signal;

an adaptive filter unit configured to operate by receiving a composite signal of the difference signal and another signal as an input signal; and a unit configured to calculate an error signal between an output signal of the adaptive filter unit and a signal having correlation with the another signal being set as a desired signal, wherein characteristics of the adaptive filter are changed by using the error signal, and characteristics of the variable filter are changed in accordance with a change in the characteristics of the adaptive filter.

3. A noise eliminating device comprising:

a calculator configured to calculate a signal relating to a noise component from an input signal in which a noise is mixed in a target signal;

a first non-linear processor configured to perform a non-linear process on an output signal of the calculation unit;

a variable filter unit configured to process a signal relating to the input signal and output a processed signal;

a second non-linear processor configured to perform a non-linear process on a signal relating to the input signal;

an adaptive filter unit configured to operate by receiving an output signal of the second non-linear processing unit as an input signal; and a unit configured to calculate an error signal between an output signal of the adaptive filter unit and a delayed signal of a composite signal of an output signal of the first non-linear processing unit and the output signal of the second non-linear processing unit being set as a desired signal, wherein characteristics of the adaptive filter are changed by using the error signal, and characteristics of the variable filter are changed in accordance with a change in the characteristics of the adaptive filter.

4. The noise eliminating device according to claim 3, wherein the first non-linear processing unit and the second non-linear processing unit perform square calculating processes or absolute value calculating processes.

5. A noise eliminating device comprising:

a calculator configured to calculate a signal relating to a noise component from an input signal in which a noise is mixed in a target signal;

a first non-linear processor configured to perform a non-linear process on an output signal of the calculation unit;

a variable filter unit configured to process a signal relating to the input signal and output a processed signal;

a second non-linear processor configured to perform a non-linear process on a signal relating to the input signal;

an adaptive filter unit configured to operate by receiving a composite signal of an output signal of the first non-linear processing unit and an output signal of the second non-linear processing unit as an input signal; and a unit configured to calculate an error signal between an output signal of the adaptive filter unit and a delayed signal of the output signal of the second non-linear processing unit being set as a desired signal, wherein characteristics of the adaptive filter are changed by using the error signal, and characteristics of the variable filter are changed in accordance with a change in the characteristics of the adaptive filter.

6. The noise eliminating device according to claim 5, wherein the first non-linear processing unit and the second non-linear processing unit perform square calculating processes or absolute value calculating processes.

7. A noise eliminating device comprising:

a signal calculator that calculates a difference signal between a signal of one channel out of a plurality of signals input from a plurality of channels and a signal of another channel;

a first non-linear processor configured to perform a non-linear process on the difference signal;

a variable filter unit configured to process the signals of the plurality of channels and output processed signals;

a second non-linear processor configured to perform a non-linear process on the signal of the one channel or a sum signal of the signal of the one channel and the signal of another channel;

an adaptive filter unit configured to operate by receiving a composite signal of an output signal of the first non-linear processing unit and an output signal of the second non-linear processing unit as an input signal; and a unit configured to calculate an error signal between an output signal of the adaptive filter unit and a delayed signal of the output signal of the second non-linear processing unit being set as a desired signal, wherein characteristics of the adaptive filter are changed by using the error signal, and characteristics of the variable filter are changed in accordance with a change in the characteristics of the adaptive filter.

8. The noise eliminating device according to claim 7, wherein the first non-linear processing unit and the second non-linear processing unit perform square calculating processes or absolute value calculating processes.

9. A noise eliminating device comprising:

a signal calculator that calculates a difference signal and a sum signal between a signal of one channel out of a plurality of signals input from a plurality of channels and a signal of another channel;

a first non-linear processor configured to perform a non-linear process on the difference signal;

a variable filter unit configured to process the sum signal and output a processed signal;

a second non-linear processor configured to perform a non-linear process on the signal of the one channel or the sum signal;

an adaptive filter unit configured to operate by receiving a composite signal of an output signal of the first non-linear processing unit and an output signal of the second non-linear processing unit as an input signal; and a unit configured to calculate an error signal between an output signal of the adaptive filter unit and a delayed signal of the output signal of the second non-linear processing unit being set as a desired signal, wherein characteristics of the adaptive filter are changed by using the error signal, and characteristics of the variable filter are changed in accordance with a change in the characteristics of the adaptive filter.

10. The noise eliminating device according to claim 9, wherein the first non-linear processing unit and the second non-linear processing unit perform square calculating processes or absolute value calculating processes.

11. A noise eliminating device comprising:

a signal calculator that calculates a difference signal between a signal of one channel out of a plurality of signals input from a plurality of channels and a signal of another channel;

a first non-linear processor configured to perform a non-linear process on the difference signal;

a variable filter unit configured to process the signals of the plurality of channels and output processed signals;

a second non-linear processor configured to perform a non-linear process on the signal of the one channel or a sum signal of the signal of the one channel and the signal of another channel;

an adaptive filter unit configured to operate by receiving an output signal of the second non-linear processing unit as an input signal; and a unit configured to calculate an error signal between an output signal of the adaptive filter unit and a delayed signal of a composite signal of an output signal of the first non-linear processing unit and the output signal of the second non-linear processing unit being set as a desired signal, wherein characteristics of the adaptive filter are changed by using the error signal, and characteristics of the variable filter are changed in accordance with a change in the characteristics of the adaptive filter.

12. The noise eliminating device according to claim 11, wherein the first non-linear processing unit and the second non-linear processing unit perform square calculating processes or absolute value calculating processes.

13. A noise eliminating device comprising:

a signal calculator that calculates a difference signal and a sum signal between a signal of one channel out of a plurality of signals input from a plurality of channels and a signal of another channel;

a first non-linear processor configured to perform a non-linear process on the difference signal;

a variable filter unit configured to process the sum signal and output a processed signal;

a second non-linear processor configured to perform a non-linear process on the signal of the one channel or the sum signal;

an adaptive filter unit configured to operate by receiving an output signal of the second non-linear processing unit as an input signal; and a unit configured to calculate an error signal between an output signal of the adaptive filter unit and a delayed signal of a composite signal of an output signal of the first non-linear processing unit and the output signal of the second non-linear processing unit being set as a desired signal, wherein characteristics of the adaptive filter are changed by using the error signal, and characteristics of the variable filter are changed in accordance with a change in the characteristics of the adaptive filter.

14. The noise eliminating device according to claim 13, wherein the first non-linear processing unit and the second non-linear processing unit perform square calculating processes or absolute value calculating processes.

15. A noise eliminating method comprising:

calculating a difference signal between a signal of one channel out of a plurality of signals input from a plurality of channels and a signal of another channel;

performing a variable filter process in which the signals of the plurality of channels are processed and processed signals are output;

calculating a composite signal of the difference signal and another signal;

performing an adaptive filter process in which the composite signal is processed as an input signal and output a processed signal;

calculating an error signal between an output signal of an adaptive filter and a signal having correlation with the another signal being set as a desired signal;

changing characteristics of the adaptive filter by using the error signal; and changing characteristics of the variable filter in accordance with a change in the characteristics of the adaptive filter.

16. A noise eliminating program that allows a computer to perform the noise eliminating method according to claim 15.

17. A noise eliminating device comprising:

a first sound collecting unit configured to acquire a first audio signal;

a second sound collecting unit configured to acquire a second audio signal;

a first calculator configured to calculate a first difference signal that is a difference between a component of a first frequency band of the first audio signal and a component of the first frequency band of the second audio signal and a first sum signal that is a sum thereof;

a second calculator configured to calculate a second difference signal that is a difference between a component of a second frequency band of the first audio signal and a component of the second frequency band of the second audio signal and a second sum signal that is a sum thereof;

a first noise reduction processor configured to perform a first noise reducing process for the first audio signal and the second audio signal and output a first reduction processing signal;

a second noise reduction processing unit that perform a second noise reducing process for the first audio signal and the second audio signal and output a second reduction processing signal;

a switching unit that selects and outputs either the first reduction processing signal or the second reduction processing signal;

a first controller configured to determine whether or not the first reduction processing signal is selected based on the amplitude of the first difference signal and the amplitude of the first sum signal and perform control of the switching unit to output the first reduction processing signal in a case when the first reduction processing signal is determined to be selected; and a second controller configured to control the second noise reduction processing unit based on the amplitude of the second difference signal and the amplitude of the second sum signal.

18. The noise eliminating device according to claim 17, wherein the second control unit controls the second noise reduction processing unit based on the amplitude of the first difference signal, the amplitude of the first sum signal, the amplitude of the second difference signal, and the amplitude of the second sum signal.

19. A noise eliminating device comprising:

a first sound collecting unit configured to acquire a first audio signal;

a second sound collecting unit configured to acquire a second audio signal;

a first calculator configured to calculate a first difference signal that is a difference between a component of a first frequency band of the first audio signal and a component of the first frequency band of the second audio signal and a first sum signal that is a sum thereof;

a first noise reduction processor configured to perform a first noise reducing process for the first audio signal and the second audio signal and outputs a first reduction processing signal;

a switching unit configured to select the first reduction processing signal or the first audio signal and the second audio signal and outputs a first post-selection signal and a second post-selection signal;

a first controller configured to determine whether to select the first reduction processing signal based on the amplitude of the first difference signal and the amplitude of the first sum signal and perform control of the switching unit to output the first reduction processing signal in a case when the first reduction processing signal is determined to be selected;

a unit configured to calculate a second difference signal that is a difference between a component of a second frequency band of the first post-selection signal and a component of the second frequency band of the second post-selection signal and a second sum signal that is a sum thereof;

a second noise reducing unit configured to perform a second noise reducing process for the first post-selection signal and the second post-selection signal; and a second controller configured to control the second noise reducing unit based on the amplitude of the second difference signal and the amplitude of the second sum signal.

20. A noise eliminating method comprising:

calculating a first difference signal that is a difference between a component of a first frequency band of a first audio signal of one channel out of a plurality of audio signals input from a plurality of channels and a component of the first frequency band of a second audio signal of another channel and a first sum signal that is a sum thereof;

calculating an amplitude of the first difference signal;

calculating an amplitude of the first sum signal;

calculating a second difference signal that is a difference between a component of a second frequency band of the first audio signal and a component of the second frequency band of the second audio signal and a second sum signal that is a sum thereof;

calculating an amplitude of the second difference signal;

calculating an amplitude of the second sum signal;

calculating a first reduction processing signal by performing a first noise reducing process for the first audio signal and the second audio signal;

calculating a second reduction processing signal by performing a second noise reducing process for the first audio signal and the second audio signal;

selecting and outputting either the first reduction processing signal or the second reduction processing signal;

determining whether or not the first reduction processing signal is selected based on the amplitude of the first difference signal and the amplitude of the first sum signal and performing control to output the first reduction processing signal in a case when the first reduction processing signal is determined to be selected; and controlling the second noise reducing process based on the amplitude of the second difference signal and the amplitude of the second sum signal.

21. A noise eliminating program that allows a computer to perform the noise eliminating method according to claim 20.

* * * * *